US008680047B2

(12) United States Patent
Greene et al.

(10) Patent No.: US 8,680,047 B2
(45) Date of Patent: Mar. 25, 2014

(54) FAS PEPTIDE MIMETICS AND USES THEREOF

(75) Inventors: Mark I. Greene, Penn Valley, PA (US); Ramachandran Murali, Drexel Hill, PA (US); Akihiro Hasegawa, Chiba (JP)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 13/210,117

(22) Filed: Aug. 15, 2011

(65) Prior Publication Data

US 2012/0245081 A1 Sep. 27, 2012

Related U.S. Application Data

(60) Division of application No. 11/869,556, filed on Oct. 9, 2007, now Pat. No. 8,022,176, which is a continuation of application No. 10/445,399, filed on May 23, 2003, now Pat. No. 7,288,519.

(60) Provisional application No. 60/383,309, filed on May 23, 2002, provisional application No. 60/465,943, filed on Apr. 28, 2003.

(51) Int. Cl.
*A61K 38/00* (2006.01)

(52) U.S. Cl.
USPC .......................................................... 514/4.3

(58) Field of Classification Search
None
See application file for complete search history.

(56) References Cited

U.S. PATENT DOCUMENTS

| | | | |
|---|---|---|---|
| 2,738,366 | A | 3/1956 | Vassel |
| 4,215,051 | A | 7/1980 | Schroeder et al. |
| 4,522,918 | A | 6/1985 | Schlom et al. |
| 4,946,778 | A | 8/1990 | Ladner et al. |
| 5,328,985 | A | 7/1994 | Sano et al. |
| 5,334,702 | A | 8/1994 | Greene et al. |
| 5,338,532 | A | 8/1994 | Tomalia et al. |
| 5,470,571 | A | 11/1995 | Herlyn et al. |
| 5,480,968 | A | 1/1996 | Kraus et al. |
| 5,632,994 | A | 5/1997 | Reed et al. |
| 5,637,677 | A | 6/1997 | Greene et al. |
| 5,663,144 | A | 9/1997 | Greene et al. |
| 5,665,539 | A | 9/1997 | Sano et al. |
| 5,677,171 | A | 10/1997 | Hudziak et al. |
| 5,705,157 | A | 1/1998 | Greene |
| 5,720,954 | A | 2/1998 | Hudziak et al. |
| 5,725,856 | A | 3/1998 | Hudziak et al. |
| 5,747,245 | A | 5/1998 | Reed et al. |
| 5,770,195 | A | 6/1998 | Hudziak et al. |
| 5,772,997 | A | 6/1998 | Hudziak et al. |
| 5,811,098 | A | 9/1998 | Plowman et al. |
| 5,821,337 | A | 10/1998 | Carter et al. |
| 5,869,445 | A | 2/1999 | Cheever et al. |
| 5,874,400 | A | 2/1999 | Sundelin et al. |
| 5,919,764 | A | 7/1999 | Greene et al. |
| 5,922,553 | A | 7/1999 | Eberwine et al. |
| 5,968,511 | A | 10/1999 | Akita et al. |
| 5,995,311 | A | 11/1999 | Kuwano |
| 6,015,567 | A | 1/2000 | Hudziak et al. |
| 6,022,523 | A | 2/2000 | Degrado et al. |
| 6,054,297 | A | 4/2000 | Carter et al. |
| 6,100,377 | A | 8/2000 | Greene |
| 6,165,464 | A | 12/2000 | Hudziak et al. |
| 6,252,050 | B1 | 6/2001 | Ashkenazi et al. |
| 6,265,535 | B1 | 7/2001 | Greene et al. |
| 6,342,219 | B1 | 1/2002 | Thorpe et al. |
| 6,391,590 | B1 | 5/2002 | Sano et al. |
| 6,413,934 | B1 | 7/2002 | Stayton et al. |
| 6,417,168 | B1 | 7/2002 | Greene et al. |
| 6,451,995 | B1 | 9/2002 | Cheung et al. |
| 6,497,881 | B1 | 12/2002 | Meruelo et al. |
| 6,548,634 | B1 | 4/2003 | Ballinger et al. |
| 6,627,196 | B1 | 9/2003 | Baughman et al. |
| 6,743,592 | B1 | 6/2004 | Greene et al. |
| 6,790,614 | B1 | 9/2004 | Pippig et al. |
| 6,949,245 | B1 | 9/2005 | Sliwkowski |
| 7,020,563 | B1 | 3/2006 | Bentley et al. |
| 7,045,286 | B2 | 5/2006 | Greene et al. |
| 7,144,991 | B2 | 12/2006 | Goshorn et al. |
| 7,288,519 | B2 | 10/2007 | Greene et al. |
| 7,638,598 | B2 | 12/2009 | Greene et al. |
| 7,662,374 | B2 | 2/2010 | Greene et al. |
| 7,781,566 | B2 | 8/2010 | Greene et al. |
| 7,906,624 | B2 | 3/2011 | Greene et al. |
| 8,022,176 | B2 | 9/2011 | Greene et al. |

(Continued)

FOREIGN PATENT DOCUMENTS

| | | |
|---|---|---|
| JP | 2002-114800 | 4/2002 |
| JP | 2002-138099 | 5/2002 |

(Continued)

OTHER PUBLICATIONS

Agus et al., "Targeting ligand-activated ErbB2 signaling inhibits breast and prostate tumor growth", Cancer Cell, Aug. 2002, 2(2), 127-137.
Ahmed et al., "Nonenzymic reactivation of reduced bovine pancreatic ribonuclease by air oxidation and by glutathione oxidoreduction buffers", J. Biol. Chem., Nov. 1975, 250(21), 8477-8482.
Albericio, "Improved approach for anchoring Nα-9-fluorenylmethyloxycarbonylamino acids as p-alkoxybenzyl esters in solid-phase peptide synthesis", Int. J. Peptide Protein Res., Jul. 1985, 26(1), 92-97.
Alroy et al., "The ErbB signaling network in embryogenesis and oncogenesis: signal diversification through combinatorial ligand-receptor interactions", FEBS Letters, Jun. 23, 1997, 410(1), 83-86.

(Continued)

*Primary Examiner* — Thomas Heard
(74) *Attorney, Agent, or Firm* — Baker & Hostetler LLP

(57) ABSTRACT

Exocyclic peptide mimetics that disable Fas were developed. A three dimensional model of the Fas receptor-ligand complex was constructed and structurally predicted regions of the receptor that were relevant to binding ligand were used to create constrained peptide mimetics. Exocyclic anti-Fas peptide mimetics were identified that block Fas receptor-ligand interactions, and modulate Fas biological activity both in vitro and in vivo. The mimetics are useful, e.g., for treating Fas-related pathologies.

22 Claims, 6 Drawing Sheets

(56) References Cited

U.S. PATENT DOCUMENTS

| | | |
|---|---|---|
| 8,057,799 B2 | 11/2011 | Greene et al. |
| 2002/0094534 A1 | 7/2002 | Greene et al. |
| 2003/0148932 A1 | 8/2003 | Greene et al. |
| 2004/0132641 A1 | 7/2004 | Greene et al. |
| 2006/0280748 A1 | 12/2006 | Buckheit |
| 2010/0076174 A1 | 3/2010 | Greene et al. |

FOREIGN PATENT DOCUMENTS

| | | |
|---|---|---|
| WO | WO 98/17797 | 4/1998 |
| WO | WO 98/53842 | 12/1998 |
| WO | WO 99/33965 | 7/1999 |
| WO | WO 99/65935 | 1/2000 |
| WO | WO 01/00244 | 1/2001 |
| WO | WO 02/66980 | 8/2002 |
| WO | WO 02/081649 | 10/2002 |
| WO | WO 03/099845 | 12/2003 |
| WO | WO 2005/081898 | 9/2005 |
| WO | WO 2009/089362 | 7/2009 |

OTHER PUBLICATIONS

Argarana, et al., "Molecular cloning and nucleotide sequence of the streptavidin gene", Nucleic Acids Res., Feb. 1986, 14(4), 1871-1882.

Bach et al., "Structural Studies of a Family of High Affinity Ligands for GPIIb/IIIa", J. of American Chemical Society, Apr. 1994, 116(8), 3207-3219.

Bajorath et al. "Analysis of fas-ligand interactions using a molecular model of the receptor-ligand interface", J. of Computer-aided Molecular Design, Jul. 1999, 13(4), 409-418.

Banner et al., "Crystal Structure of the Soluble Human 55 kd TNF Receptor-Human TNF β Complex: Implications For TNF Receptor Activation", Cell, May 7, 1993, 73(3), 431-445.

Barrios et al., "Length of the antibody heavy chain complementarity determining region 3 as a specificity-determining factor", J. Molecular Recognition, Jul./Aug. 2004, 17(4), 332-338.

Baselga et al., "Recombinant Humanized Anti-HER2 Antibody (Herceptin) Enhances the Antitumor Activity of Paclitaxel and Doxorubicin Against HER2/neu Overexpressing Human Breast Cancer Xenografts", Cancer Research, Jul. 1, 1998, 58(13), 2825-2831.

Beltinger et al,. "Mutation analysis of CD95 (APO-1/Fas) in childhood B-lineage acute lymphoblastic leukaemia", British Journal of Hematology, Aug. 1998, 102(3), 722-728.

Benkirane et al., "Exploration of Requirements for Peptidomimetic Immune Recognition", J. Biol. Chem., Dec. 1996, 271, 33218-33224.

Beneviste et al., "Structure-activity analysis of binding kinetics for NMDA receptor competitive antagonists: the influence of conformational restriction", Br. J. Pharmacol., Sep. 1991, 104(1), 207-221.

Berezov et al., "Disabling Receptor Ensembles with Rationally Designed Interface Peptidomimetics", The Journal of Biological Chemistry, Aug. 2, 2002, 277(31), 28330-28339.

Berezov et al., "Disabling ErbB Receptors with Rationally Designed Exocyclic Mimetics of Antibodies: Structure-Function Analysis", J. of Medicinal Chemistry, Aug. 2, 2001, 44(16), 2565-2574.

Bernstein et al., "The protein data bank: A computer-based archival file for macromolecular structures," Eur. J. Biochem., Nov. 1977, 80(2), 319-324.

Biancone et al., "Development of Inflammatory Angiogenesis by Local Stimulation of Fas In Vivo", J. Exp. Med., Jul. 1997, 186, 147-152.

Bishayee et al., "Phosphorylation of Tyrosine 992, 1068, and 1086 Is Required for Conformational Change of the Human Epidermal Growth Factor Receptor C-Terminal Tail", Molecular Biology of the Cell, Mar. 1999, 10, 525-536.

Bishayee et al., "Role of conformational alteration in the epidermal growth factor receptor (EGFR) function", Biochemical Pharmacology, Oct. 2000, 60(8), 1217-1223.

Blain et al., "Differential interaction of the cyclin-dependent kinase (Cdk) inhibitor p27Kip1 with cyclin A-Cdk2 and cyclin D2-Cdk4", J. Bio. Chem., Oct. 10, 1997, 272(41), 25863-25872.

Borgelt et al., "The Palliation of Brain Metastases: Final Results of the First Two Studies by the Radiation Therapy Oncology Group", Int. J. Radiat Oncol. Biol. Phys., Jan. 1980, 6(1), 1-9.

Brennan et al., "HER2/Neu: mechanisms of dimerization/oligomerization", Oncogene, Dec. 11, 2000, 19(53), 6093-6101.

Brisson et al., "Expression of a bacterial gene in plants by using a viral vector", Nature, Aug. 1984, 310, 511-514.

Britsch et al., "The ErbB2 and ErbB3 receptors and their ligand, neuregulin-1, are essential for development of the sympathetic nervous system", Genes Dev., Jun. 15, 1998, 12(12), 1825-1836.

Broglie et al., "Light-Regulated Expression of a Pea Ribulose-1,5-Bisphosphate Carboxylase Small Subunit Gene in Transformed Plant Cells", Science, May 1984, 224, 838-843.

Brown et al., "Demonstration By Two-Color Flow Cytometry That Tyrosine Kinase Activity Is Required For Down-Modulation of the Oncogenic neu Receptor", DNA Cell Biology, Feb. 1994, 13(2), 193-209.

Bruccoleri et al., "Structure of antibody hypervariable loops reproduced by a conformational search algorithm", Nature, Oct. 1988, 335, 564-568.

Brunger, A. T., "A System for X-ray Crystallography and NMR," X-PLOR Version 3.1, Yale University Press, 1992, 435 pages.

Burgess et al., "Solid Phase Syntheses of Oligoureas", J. American Chemical Society, Feb. 19, 1997, 119(7), 1556-1564.

Burgess et al., "Solid phase syntheses of peptidomimetics," American Chemical Society, Abstracts of Papers Part 2, 212th ACS National Meeting, Aug. 25-29, 1996, ORGN-157.

Burgess et al., "Possible Dissociation of the Heparin-Binding and Mitogenic Activities of Heparin-Binding (Acidic Fibroblast) Growth Factor-1 From Its Receptor-Binding Activities By Site-Directed Mutagenesis of a Single Lysine Residue", J. of Cell Biology, Nov. 1, 1990, 111(5), 2129-2138.

Cambier, "Inhibitory Receptors Abound", Proc. Natl. Acad. Sci. USA, Jun. 10, 1997, 94(12), 5993-5995.

Capone et al., "Relationship Between Antigen Density and Immunotherapeutic Response Elicited By Monoclonal Antibodies against solid tumors", JNCI, Mar. 1984, 72(3), 673-677.

Carraway et al., "A neu acquaintance for erbB3 and erbB4: a role for receptor heterodimerization in growth signaling", Cell, Jul. 15, 1994, 78(1), 5-8.

Carraway et al., "Location of the Epidermal Growth Factor Binding Site On the EGF Receptor: A Resonance Energy Transfer Study", Biochemistry, Sep. 1990, 29(37), 8741-8747.

Carter et al., "Humanization of an Anti-p185HER2 Antibody For Human Cancer Therapy", Proc. Natl. Acad. Sci. USA, May 15, 1992, 89(10), 4285-4289.

Chang et al., "Ligands for ErbB-family receptors encoded by a neuregulin-like gene", Nature, May 29, 1997, 387(6632), 509-512.

Chen et al., "Regulation of the Proinflammatory Effects of Fas Ligand (CD95L)", Science, Nov. 1998, 282(5394), 1714-1717.

Chiri et al., "Evidence for MAP kinase activation during mitotic division", J. Cell Sci., Sep. 1998, 111, 2519-2527.

Chirinos-Rojas al., "A peptidomimetic antagonist of TNF-alpha-mediated cytotoxicity identified from a phage-displayed random peptide library," J. Immunol., Nov. 1998, 161(10), 5621-5626.

Cho et al., "Macromolecular versus smallmolecule therapeutics: drug discovery, development and clinical considerations", Trends Biotechnol., May 1996, 14(5), 153-158.

Chothia et al., "Canonical structures for the hypervariable regions of immunoglobulins", J. Mol. Biol., Aug. 20, 1987, 196(4), 901-917.

Christodoulides et al., "Immunization With Synthetic Peptides Containing Epitopes of the Class 1 Outer-Membrane Protein of Neisseria meningitidis: Production of Bactericidal Antibodies On Immunization With A Cyclic Peptide", J. of General Microbiology, Aug. 1993, 139(8), 1729-1738.

Chung et al., "Inhibition of Fas signaling prevents hepatic injury and improves organ blood flow during sepsis," Surgery, Aug. 2001, 130(2), 339-345.

(56) References Cited

OTHER PUBLICATIONS

Cohen et al., "A Native 170,000 Epidermal Growth Factor Receptor-Kinase Complex From Shed Plasma Membrane Vesicles", J. of Biological Chemistry, Feb. 10, 1982, 257(3), 1523-1531.

Cole et al., "The EBV-hybridoma technique and its application to human lung cancer", Monoclonal Antibodies and Cancer Therapy, 1985, 77-96.

Coruzzi et al., "Tissue-specific and light-regulated expression of a pea nuclear gene encoding the small subunit of ribulose-1,5-bisphosphate carboxylase", EMBO J., Aug. 1984, 3(8), 1671-1679.

Cote et al., "Generation of human monoclonal antibodies reactive with cellular antigens", PNAS, Apr. 1983, 80(7), 2026-2030.

Daeron et al., "The same tyrosine-based inhibition motif, in the intracytoplasmic domain of Fc gamma RIIB, regulates negatively BCR-, TCR-, and FcR- dependent cell activation", Immunity, Nov. 1995, 3(5), 635-646.

Dahia et al., "Mutation and expression analysis of the p27/kip1 gene in corticotrophin-secreting tumours", Oncogene, Jan. 8, 1998, 16(1), 69-76.

D'Ambrosio et al., "The SHIP phosphatase becomes associated with Fc gammaRIIB1 and is tyrosine phosphorylated during 'negative' signaling", Immunology Letters, Dec. 1996, 54(2-3), 77-82.

Davies et al., "Antibody VH Domains As Small Recognition Units", Nature Biotechnology, May 1995, 13(5), 475-479.

Davies et al., "Single Antibody Domains As Small Recognition Units: Design and in vitro Antigen Selection of Camelized, Human VH Domains With Improved Protein Stability", Protein Engineering Design and Selection, Jun. 1996, 9(16), 531-537.

Dawson et al., "Pigment Epithelium-Derived Factor: A Potent Inhibitor of Angiogenesis", Science, Jul. 1999, 285(5425), 245-248.

DeFouw et al., "Mapping of the microcirculation in the chick chorioallantoic membrane during normal angiogenesis", Microvasc. Res., Sep. 1989, 38(2), 136-147.

Deb et al., "A common requirement for the catalytic activity and both SH2 domains of SHP-2 in mitogen-activated protein (MAP) kinase activation by the ErbB family of receptors. A specific role for SHP-2 in map, but not c-Jun amino-terminal kinase activation", J. Biol. Chem., Jul. 3, 1998, 273(27), 16643-16646.

Decanniere et al., "A Single-Domain Antibody Fragment In Complex With RNase A: Non-Canonical Loop Structures and Nanomolar Affinity Using Two CDR Loops", Structure, Apr. 15, 1999, 7(4), 361-370.

Dermer, G. B., "Another anniversary for the war on cancer", BioTechnology, Mar. 1994, 12, 320.

Deveraux et al., "X-linked Iap is a direct inhibitor of cell-death proteases", Nature, Jul. 17, 1997, 388(6639), 300-304.

DiCristofano et al., "Impaired Fas response and autoimmunity in Pten+/− mice", Science, Sep. 24, 1999, 285(5436), 2122-2125.

DiCristofano et al., "The multiple roles of PTEN in tumor suppression", Cell, Feb. 18, 2000, 100(4), 387-390.

DiBlasio et al., "Noncoded Residues as Building Blocks in the Design of Specific Secondary Structures: Symmetrically Disubstituted Glycines and 13-Alanine", Biopolymers, Jul. 1993, 3(7)3, 1037-1049.

DiFiore et al., "ErbB-2 Is a Potent Oncogene When Overexpressed in NIH/3T3 Cells", Science, Jul. 1987, 237, 178-182.

Doherty et al., "The HER-2/neu Receptor Tyrosine Kinase Gene Encodes A Secreted Autoinhibitor", PNAS, Sep. 14, 1999, 96(19), 10869-10874.

Dougall et al., "The neu-Oncogene: Signal Transduction Pathways, Transformation Mechanisms and Evolving Therapies", Oncogene, Aug. 1994, 9(8), 2109-2123.

Doughty et al., "sFas and sFas Ligand and Pediatric Sepsis-Induced Multiple Organ Failure Syndrome", Pediatr. Res., Dec. 2002, 52(6), 922-927.

Drebin et al., "Development of Monoclonal Antibodies Reactive With the Product of the neu Oncogene", Symposium on Fundamental Cancer Research, 1986, 38, 277-289.

Drebin et al., "Down-modulation of an oncogene protein product and reversion of the transformed phenotype by monoclonal antibodies", Cell, Jul. 1985, 41(13), 695-706.

Drebin et al., "Inhibition of Tumor Growth By A Monoclonal Antibody Reactive With An Oncogene-Encoded Tumor Antigen", Proc. Natl. Acad. Sci. USA, Dec. 1, 1986, 83(23), 9129-9133.

Drebin et al., "Monoclonal antibodies identify a cell-surface antigen associated with an activated cellular oncogene", Nature, Dec. 6-12, 1984, 312(5994), 545-548.

Drebin et al., "Monoclonal antibodies reactive with distinct domains of the neu oncogene-encoded p185 molecule exert synergistic anti-tumor effects in vivo", Oncogene, Mar. 1988, 2(3), 273-277.

Dubel et al., "Bifunctional and multimeric complexes of streptavidin fused to single chain antibodies (scFv)", J. Immunol. Methods, Jan. 1995, 178(2), 201-209.

Dudek et al., "Regulation of neuronal survival by the serine-threonine protein kinase Akt", Science, Jan. 31, 1997, 275(5300), 661-665.

Dumoulin et al., "Single-Domain Antibody Fragments With High Conformational Stability", Protein Science, Mar. 2002, 11(3), 500-515.

Eck et al., "The Structure of Human Lymphotoxin (Tumor Necrosis Factor-$\beta$) At 1.9-Å Resolution", J. of Biological Chemistry, Feb. 5, 1992, 267(4), 2119-2122.

Eck et al., "The Structure of Tumor Necrosis Factor-$\alpha$ At 2.6 Å Resolution: Implications Or Receptor Binding", J. of Biological Chemistry, Oct. 10, 1989, 264(29), 17595-17605.

Eigenbrot et al., "X-ray structures of fragments from binding and nonbinding versions of a humanized anti-CD18 antibody: structural indications of the key role of VH residues 59 to 65", Proteins, Jan. 1994, 18(1), 49-62.

Eigenbrot et al., "X-ray structures of the antigen-binding domains from three variants of humanized anti-p185HER2 antibody 4D5 and comparison with molecular modeling", J. Mol. Biology, Feb. 20, 1993, 229(4), 969-995.

Erickson et al., "ErbB3 is required for normal cerebellar and cardiac development: a comparison with ErbB2-and heregulin-deficient mice", Development, Dec. 1997, 124(24), 4999-5011.

Ettmayer et al., "Lessons Learned from Marketed and Investigational Prodrugs," J. Med. Chem., May 6, 2004, 47(10), 2393-2404, Prodrugs are often accidental discoveries.

European Supplementary Search Report dated Apr. 20, 2006 for European Patent Application No. 03729102.8, 3 pages.

Famularo et al., "Fas/Fas ligand on the road: an apoptotic pathway common to AIDS, autoimmunity, lymphoproliferation and transplantation", Medical Hypothesis, Jul. 1999, 53(1), 50-62.

Felix et al., "Applications of BOP reagent in solid phase synthesis", Int. J. Pep. Prot. Res., Feb. 1988, 31(2), 231-238.

Fendly et al, "Characterization of Murine Monoclonal Antibodies Reactive to Either the Human Epidermal Growth Factor Receptor or HER2/neu Gene Product", Cancer Research, Mar. 1, 1990, 50, 1550-1558.

Feng, "Shp-2 tyrosine phosphatase: signaling one cell or many", Exp. Cell Res., Nov. 25, 1999, 253(1), 47-54.

Ferguson et al., "Extracellular Domains Drive Homo- But Not Hetero-Dimerization of erbB Receptors", EMBO J., Sep. 1, 2000, 19(17), 4632-4643.

Fernandez-Pol, "Epidermal Growth Factor Receptor of A431 Cells—Characterization of a monoclonal anti-receptor antibody noncompetitive agonist of epidermal growth factor action", Biological Chemistry, Apr. 25, 1985, 260(8), 5003-5011.

Fingl et al., "The Pharmacological Basis of Therapeutics," 1975, Chapter 1, p. 1.

Florsheimer et al., "Solid-phase synthesis of peptides with highly acid-sensitive HMPB linker," Peptides, Proceedings of the 21st European Peptide Symposium, Giralt, E. and Andreu, D., eds., ESCOM Science Publishers, The Netherlands, 1991, 131-133.

Fujioka et al., "A novel membrane glycoprotein, SHPS-1, that binds the SH2-domain-containing protein tyrosine phosphatase SHP-2 in response to mitogens and cell adhesion", Molecular and Cellular Biology, Dec. 1996, 16(12), 6887-6899.

Furnari et al., "Growth suppression of glioma cells by PTEN requires a functional phosphatase catalytic domain", Proc. Natl. Acad. Sci. USA, Nov. 11, 1997, 94(23), 12479-12484.

(56) References Cited

OTHER PUBLICATIONS

Furnari et al., "The phosphoinositol phosphatase activity of PTEN mediates a serum-sensitive G1 growth arrest in glioma cells", Cancer Research, Nov. 15, 1998, 58(22), 5002-5008.

Gainer et al., "Gene Gun Transfection of Human Glioma and Melanoma Cell Lines With Genes Encoding Human IL-12 and GM-CSF", J. Neuro-Oncology, Mar. 2000, 47(1), 23-30.

Gantner et al., "Concanavalin A—induced T-cell—mediated hepatic injury in mice: The role of tumor necrosis factor," Hepatology, Jan. 1995, 21(1), 190-198.

Gantner et al., "T Cell Stimulus-Induced Crosstalk between Lymphocytes and Liver Macrophages Results in Augmented Cytokine Release", Exp. Cell. Res., Nov. 1996, 229(1), 137-146.

Gao et al., "Antiinflammatory Effects of CD95 Ligand (FasL)-induced Apoptosis", J. Exp. Med., Sep. 1998, 188, 887-896.

Garrett et al., "Crystal Structure of the First Three Domains of the Type-1 Insulin-Like Growth Factor Receptor", Nature, Jul. 23, 1998, 394(6691), 395-399.

Gasparini et al., "Human Breast Cancer—Prognostic Significance of the c-erbB-2 Oncoprotein Compared with Epidermal Growth Factor Receptor, DNA Ploidy, and Conventional Pathologic Features", J. of Clinical Oncology, May 1992, 10(5), 686-695.

Gavrieli et al., "Identification of programmed cell death in situ via specific labeling of nuclear DNA fragmentation", J. Cell Biol., Nov. 1992, 119(3), 493-501.

Gettins et al., "Pigment Epithelium-Derived Factor (PEDF), a Serpin with Potent Anti-Angiogenic and Neurite Outgrowth-promoting Properties," Biol. Chem., Nov. 2002, 383(11), 1677-1682.

Gilhar et al., "Mediation of alopecia areata by cooperation between CD4+ and CD8+ T lymphocytes: transfer to human scalp explants on Prkdc(scid) mice," Arch. Dermatol., Jul. 2002, 138(7), 916-922.

Gill et al., "Calculation of Protein Extinction Coefficients From Amino Acid Sequence Data", Analytical Biochemistry, Nov. 1, 1989, 182(2), 319-326.

Goodman et al., "Peptidomimetic Building Blocks For Drug Discovery: an Overview", Pure & Applied Chemistry, 1996, 68(6), 1303-1308.

Gorczyca et al., "Detection of DNA Strand Breaks in Individual Apoptotic Cells by the in Situ Terminal Deoxynucleotidyl Transferase and Nick Translation Assays", Cancer Res., Apr. 1993, 53, 1945-1951.

Goto et al., "Immunological diagnosis of Werner syndrome by down-regulated and truncated gene products," Hum. Genet., Oct. 1999, 105(4), 301-307.

Greil et al., "On the Role and Significance of Fas (Apo-1/CD95) Ligand (FasL) Expression in Immune Privileged Tissues and Cancer Cells Using Multiple Myeloma as a Model", Leukemia & Lymphoma, Nov. 1998, 31(5-6), 477-490.

Griffith et al., "CD95-Induced Apoptosis of Lymphocytes in an Immune Privileged Site Induces Immunological Tolerance", Immunity, Jul. 1996, 5, 7-16.

Griffith et al., "Fas Ligand-Induced Apoptosis as a Mechanism of Immune Privilege", Science, Nov. 1995, 270(5239), 1189-1192.

Gura et al, "Systems for Identifying New Drugs Are Often Faulty", Science, Nov. 1997, 278, 1041-1042.

Gurley et al., "Upstream sequences required for efficient expression of a soybean heat shock gene", Mol. Cell. Biol., Feb. 1986, 6(2), 559-565.

Han, H-K., "Targeted Prodrug Design to Optimize Drug Delivery," AAPS Pharmsci., Mar. 2000, 2(1), Article 6, 1-11.

Hanessian et al., "Design and Synthesis of Conformationally Constrained Amino Acids As Versatile Scaffolds and Peptide Mimetics", Tetrahedron, Sep. 22, 1997, 53(38), 12789-12854.

Honma et al., "Chromosomal instability in B-lymphoblastoid cell lines from Werner and Bloom syndrome patients," Mutat. Res., Genetic Tox. and Env. Mutagenesis, Sep. 2002, 520(1-2), 15-24.

Hansen et al., "Re-Examination and Further Development of a Precise and Rapid Dye Method For Measuring Cell Growth/Cell Kill", J. of Immunological Methods, May 12, 1989, 119(2), 203-210.

Hasegawa et al. "FAS-Disabling Small Exocyclic Peptide Mimetics Limit Apoptosis by an Unexpected Mechanism," Proceedings of the National Academy of Sciences of the United States of America, Apr. 27, 2004, 101(17), 6599-6604, XP002360129; ISSN: 0027-8424.

Hashimoto et al., "Soluble Fas ligand in the joints of patients with rheumatoid arthritis and osteoarthritis", Arthristis and Rheumatism, Apr. 1998, 41(4), 657-662.

Heldin, "Dimerization of Cell Surface Receptors In Signal Transduction", Cell, Jan. 27, 1995, 80(2), 213-223.

Hemmings, "Akt signaling: linking membrane events to life and death decisions", Science, Jan. 31, 1997, 275(5300), 628-630.

Horie et al., "Study of Disabling T-Cell Activation and Inhibiting T-Cell-Mediated Immunopathology Reveals a Possible Inverse Agonist Activity of CD4 Peptidomimetics", Exp. Mol. Pathol., Oct. 2002, 73, 93-103.

Hruby, "Conformational and Topographical Considerations in the Design of Biologically Active Peptides", Biopolymers, Jul. 1993, 33, 1073-1082.

Hruby, "Conformational restrictions of biologically active peptides via amino acid side chain groups", Life Sci., Jul. 1982, 31, 189-199.

Huang et al., "Proxy activation of protein ErbB2 by heterologous ligands implies a heterotetrameric mode of receptor tyrosine kinase interaction", Biochem. J., Apr. 1, 1998, 331(Pt. 1), 113-119.

Huang et al., "The enhanced tumorigenic activity of a mutant epidermal growth factor receptor common in human cancers is mediated by threshold levels of constitutive tyrosine phosphorylation and unattenuated signaling", J. Biol. Chem., Jan. 31, 1997, 272(5), 2927-2935.

Huse et al., "Generation of a large combinatorial library of the immunoglobulin repertoire in phage lambda," Science, Dec. 1989, 246(4935), 1275-1281.

Irmler et al., "Inhibition of death receptor signals by cellular FLIP [see comments]", Nature, Jul. 10, 1997, 388(6638), 190-195.

Jackson et al., "The Biological Action of Choriogonadotropin Is Not Dependent on the Complete Native Quaternary Interactions between the Subunits," Molecular Endocrinology, Dec. 1999, 13(12), 2175-2188.

Jackson et al., "Template-constrained cyclic peptides: design of high-affinity ligands for GPIIb/IIIa", J. of American Chemical Society, Apr. 1994, 116(18), 3220-3230.

Jacob et al., "Priming Immunization Against Cholera Toxin and E. coli Heat-Labile Toxin By A Cholera Toxin Short Peptide-Beta-Galactosidase Hybrid Synthesized In E. coli.", EMBO J., Dec. 1, 1985, 4(12), 3339-3343.

Jardines et al., "Neu(c-erbB-2/HER2) and the epidermal growth factor receptor (EGFR) in breast cancer", Pathobiology, 1993, 61(5-6), 268-282.

Jones et al., "Analysis of protein-protein interaction sites using surface patches", J. Mol. Biol., Sep. 1997, 272(1), 121-132.

Jorissen et al., "Characterization of a Comparative Model of the Extracellular Domain of the Epidermal Growth Factor Receptor", Protein Science, Feb. 2000, 9(2), 310-324.

Kakinuma et al., "Acute Toxicity of an Anti-Fas Antibody in Mice", Toxicol. Pathol., Jul. 1999, 27(4), 412-420.

Kamber et al., "The Synthesis of Cystine Peptides by Iodine Oxidation of S-Trityl-cysteine and S-Acetamidomethyl-cysteine Peptides", Helv. Chim. Acta, Jun. 1980, 63(4), 899-915.

Kanda et al., "Increased soluble Fas-ligand in sera of bone marrow transplant recipients with acute graft-versus-host disease," Bone Marrow Transplantation, Oct. 1998, 22(8), 751-754.

Kaplan et al., "Fas ligand (CD95 ligand) controls angiogenesis beneath the retina", Nat. Med., Mar. 1999, 5, 292-297.

Karp et al., "Identification of biotinylated molecules using a baculovirus-expressed luciferase-streptavidin fusion protein", Biotechniques, Mar. 1996, 20(3), 452-456, 458-459.

Kataoka et al., "Immortalization of immunologically committed Epstein-Barr virus-transformed human B-lymphoblastoid cell lines accompanied by a strong telomerase activity", Differentiation, Feb. 1998, 62(4), 203-211.

Kataoka et al., "The role of donor T cells for target organ injuries in acute and chronic graft-versus-host disease", Immunology, Jul. 2001, 103(3), 310-318.

(56) References Cited

OTHER PUBLICATIONS

Kato et al., "Elevated serum soluble Fas ligand in natural killer cell proliferative disorders", British Journal of Haematology, Dec. 1998, 103(4), 1164-1166.
Kauffmann-Zeh et al., "Suppression of c-Myc-induced apoptosis by Ras signalling through PI(3)K and PKB", Nature, Feb. 6, 1997, 385(6616), 544-548.
Kayagaki et al., "Metalloproteinase-mediated release of human Fas ligand", Dec. 1995, 182(6), 1777-1783.
Kayagaki et al., "Polymorphism of murine Fas ligand that affects the biological activity", PNAS, Apr. 1997, 94(8), 3914-3919.
Kharitonenkov et al., "A family of proteins that inhibit signalling through tyrosine kinase receptors", Nature, Mar. 13, 1997, 386(6621), 181-186.
Kieber-Emmons et al., "Therapeutic peptides and peptidomimetics", Curr. Opin. Biotechnol., Aug. 1997, 8(4), 435-441.
Kipriyanov et al., "Affinity enhancement of a recombinant antibody: formation of complexes with multiple valency by a single-chain Fv fragment-core streptavidin fusion," Protein Eng., Feb. 1996, 9(2), 203-211.
Kipriyanov et al., "Single-chain antibody streptavidin fusions: tetrameric bifunctional scFvcomplexes with biotin binding activity and enhanced affinity to antigen", Hum. Antibodies Hybridomas, 1995, 6(3), 93-101.
Kishore et al., "A recombinant homotrimer, composed of the alpha helical neck region of human surfactant protein D and C1q B chain globular domain, is an inhibitor of the classical complement pathway," J. Immunol., Jan. 2001, 166, 559-565.
Kobrin et al., "A V region mutation in a phosphocholine-binding monoclonal antibody results in loss of antigen binding", J. Immunology, Mar. 1991, 146, 2017-2020.
Kohler et al., "Continuous cultures of fused cells secreting antibody of predefined specificity," Nature, Aug. 1975, 256(5517), 495-497.
Koide et al., "DNA Vaccines", Japanese J. Pharmacol., Mar. 2000, 83(3), 167-174.
Kokai et al., "Stage-and tissue-specific expression of the neu oncogene in rat development", Proc. Natl. Acad. Sci. USA, Dec. 1987, 84(23), 8498-8501.
Kokai et al., "Synergistic Interaction of p185c-neu and the EGF Receptor Leads to Transformation of Rodent Fibroblasts", Cell, Jul. 28, 1989, 58(2), 287-292.
Koo, et al., "Development of a streptavidin-conjugated single-chain antibody that binds *Bacillus cereus* spores", App. Environ. Microbiol., Jul. 1998, 64(7), 2497-2502.
Koprowski et al., "Expression of the Receptor For Epidermal Growth Factor Correlates With Increased Dosage of Chromosome 7 In Malignant Melanoma", Somatic Cell and Molecular Genetics, May 1985, 11(3), 297-302.
Kozbor et al., "The production of monoclonal antibodies from human lymphocytes," Immunology Today, Mar. 1983, 4(3), 72-79.
Koskinen et al., "Asymmetric Intramolecular Cyclopropanation: Synthesis of Conformationally Constrained Aminocyclopropane Carboxylic Acids", ACTA Chem. Scand., 1996, 50(4), 323-327.
Kramer et al., "Neuregulins with an Ig-like domain are essential for mouse myocardial and neuronal development", Proc. Natl. Acad. Sci. USA, May 14, 1996, 93(10), 4833-4838.
Krammer, P. H., "CD95(APO-1/Fas)-Mediated Apoptosis: Live and Let Die," Adv. Immunol., 1998, 71, 163-210.
Ksontini et al., "Disparate Roles for TNF-α and Fas Ligand in Concanavalin A-Induced Hepatitis", J. Immunol., Apr. 1998, 160(8), 4082-4089.
Kuby et al, "Antigents", Immunology, Second edition, 1994, 86-96.
Kuhn et al., "Fmoc protected peptide mimetic based on a cyclohexane framework and incorporation into angiotensin II", Tetrahedron, Sep. 1997, 53(37), 12497-12504.
Kühn et al., "Fmoc Protected Peptide Mimetic Based On a Cyclohexane Framework and Incorporation Into Angiotensin II", Tetrahedron, Sep. 15, 1997, 53(37), 12497-12504.

Kumagai et al., "The Role of District p185neu Extracellular Subdomains For Dimerization With the Epidermal Growth Factor Receptor and EGF Mediated Signaling", Proc. Nat. Acad. Sci. USA, May 8, 2001, 98(10), 5526-5531.
Kuriyama et al., "Particle-Mediated Gene Transfer Into Murine Livers Using a Newly Developed Gene Gun", Gene Therapy, Jul. 2000, 7(13), 1132-1136.
Kusters et al., "Interferon gamma plays a critical role in T cell-dependent liver injury in mice initiated by concanavalin A", Gastroenterology, Aug. 1996, 111(2), 462-471.
Kusters et al., "In vivo evidence for a functional role of both tumor necrosis factor (TNF) receptors and transmembrane TNF in experimental hepatitis," Eur. J. Immunol., Nov. 1997, 27(11), 2870-2875.
Landgraf et al., "Heregulin Reverses the Oligomerization of HER3", Biochemistry, Jul. 25, 2000, 39(29), 8503-8511.
Lazar et al., "Transforming Growth Factor α: Mutation of Aspartic Acid 47 and Leucine 48 Results in Different Biological Activities", Molecular and Cellular Biology, Mar. 1988, 8(3), 1247-1252.
Le et al., "A streptavidin-cellulose-binding domain fusion protein that binds biotinylated proteins to cellulose", Enzyme Microb. Technol., Jun. 1994 16(6), 496-500.
LeBien et al., "Use of Monoclonal Antibodies, Morphology, and Cytochemistry to Probe the Cellular Heterogeneity of Acute Leukemia and Lymphoma", Cancer Res., Nov. 1981, 41, 4776-4780.
Lee et al., "Solution structure of the tetrameric minimum transforming domain of p53 ," Nature Struct. Biol., Dec. 1994, 1, 877-890.
Lee et al., "Reduced expression of the CDK inhibitor p27(KIP1) in rat two-stage bladder carcinogenesis and its association with expression profiles of p21(WAF1/Cip1) and p53", Carcinogenesis, Sep. 1999, 20(9), 1697-1708.
Lee et al., "Requirement for neuregulin receptor erbB2 in neural and cardiac development", Nature, Nov. 23, 1995, 378(6555), 394-398.
Lees, "Cyclin dependent kinase regulation", Curr. Opin., Cell Biology, Dec. 1995, 7(16), 773-780.
Leff, P., "The two-state model of receptor activation," Trends in Pharmacol. Sci., Mar. 1995, 16(3), 89-97.
Leithauser et al., "Constitutive and induced expression of APO-1, a new member of the nerve growth factor/tumor necrosis factor receptor superfamily, in normal and neoplastic cells", Lab. Invest., Oct. 1993, 69, 415-429.
Lemmon et al., "Two EGF Molecules Contribute Additively To Stabilization of the EGFR Dimer", EMBO J., Jan. 15, 1997, 16(2), 281-294.
Leszczynski et al., "Loops in globular proteins: a novel category of secondary structure," Science, Nov. 1986, 234(4778), 849-855.
Li et al., "Control of apoptosis and mitotic spindle checkpoint by surviving", Nature, Dec. 10, 1998, 396(6711), 580-584.
Li et al., "Homology Modeling Using Simulated Annealing of Restrained Molecular Dynamics and Conformational Search Calculations With CONGEN: Application In Predicting the Three-Dimensional Structure of Murine Homeodomain Msx-1", Protein Science, May 1997, 6(5), 956-970.
Li et al., "PTEN, a putative protein tyrosine phosphatase gene mutated in human brain, breast, and prostate cancer", Science, Mar. 28, 1997, 275(5308), 1943-1947.
Lippi et al., "A new colorimetric ultramicromethod for serum glutamicoxalacetic and glutamic-pyruvic transaminase determination", Clin. Chim. Acta, Jun. 1970, 28(3), 431-437.
Liu et al., "Domain-specific gene disruption reveals critical regulation of neuregulin signaling by its cytoplasmic tail", Proc. Natl. Acad. Sci. USA, Oct. 27, 1998, 95(22), 13024-13029.
Logan et al., "Adenovirus tripartite leader sequence enhances translation of mRNAs late after infection", PNAS, Jun. 1984, 81(12), 3655-3659.
Lu et al., "The PTEN/MMAC1/TEP tumor suppressor gene decreases cell growth and induces apoptosis and anoikis in breast cancer cells", Oncogene, Nov. 25, 1999, 18(50), 7034-7045.
MacCallum et al., "Antibody-antigen interactions: contact analysis and binding site topography", J. Mol. Biol., Oct. 11, 1996, 262(5), 732-745.
Mackett et al., "Vaccinia virus: a selectable eukaryotic cloning and expression vector", PNAS, Dec. 1982, 79(23), 7415-7419.

(56) References Cited

OTHER PUBLICATIONS

Mackett et al., General method for production and selection of infectious vaccinia virus recombinants expressing foreign genes, J. Virol., Mar. 1984, 49(3), 857-864.

Maggi, C. A., "Therapeutic opportunities from the pharmacological manipulation of the fas system," Pharmacological Research, Jul. 1998, 38(1), 1-34.

Magliani et al., "Therapeutic Potential of Antiidiotypic Single Chain Antibodies With Yeast Killer Toxin Activity", Nature Biotechnology, Feb. 1997, 15(2), 155-158.

Manning et al., "Design of cyclic and linear peptide antagonists of vasopressin and oxytocin: current status and future directions", Reg. Peptides, Apr. 1993, 45, 279-283.

Mariani et al., "Regulation of cell surface APO-1/Fas (CD95) ligand expression by metalloproteases", Eur. J. Immunol., Aug. 1995, 25(8), 2303-2307.

Martinez et al., "Involvement of Fas-Fas Ligand Interactions in Graft Rejection," Int. Rev. Immunol., Jan. 1999, 18(5-6), 527-546.

Matsuyama et al., "A Novel Extracellular Cyclic Lipopeptide Which Promotes Flagellum-Dependent and -Independent Spreading Growth of Serratia marcescens", J. Bacteriol., Mar. 1992, 174(6), 1769-1776.

McBride et al., "Identification of chymotrypsin inhibitors from a second-generation template assisted combinatorial peptide library", J. Pept. Sci., September, Sep. 2000, 6(9), 446-452.

McInnes et al, "Growth factor receptors: structure, mechanism, and drug discover", Biopoly, 1997, 43(5), 339-366.

McIntyre et al., "Differential expression of the cyclin-dependent kinase inhibitor P27 in primary hepatocytes in early-mid G1 and G1/S transitions", Oncogene, Aug. 12, 1999, 18(32), 4577-4585.

Meyer et al., "Multiple essential functions of neuregulin in development", Nature, Nov. 23, 1995, 378(6555), 386-390.

Mizuhara et al., "T cell activation-associated hepatic injury: mediation by tumor necrosis factors and protection by interleukin 6", J. Exp. Med., May 1994, 179(5), 1529-1537.

Mohan et al., "Apoptosis in the Cornea: Further Characterization of Fas/Fas Ligand System," Experimental Eye Research, Oct. 1997, 65(4), 575-589.

Moore, "Designing peptide mimetics", Trends Pharmacol. Sci., Apr. 1994, 15(4), 124-129.

Moosmayer et al., "Characterization of Different Soluble TNF Receptor (TNFR80) Derivatives: Positive Influence of the Intracellular Domain on Receptor/Ligand Interaction and TNF Neutralization Capacity," J. Interferon Cytokine Res., Jun. 1996, 16(6), 471-477.

Morrison et al., "Chimeric human antibody molecules: mouse antigen-binding domains with human constant region domains", PNAS, Nov. 1984, 81(21), 6851-6855.

Moscatello et al., "Constitutive activation of phosphatidylinositol 3-kinase by a naturally occurring mutant epidermal growth factor receptor", J. Biol. Chem., Jan. 2, 1998, 273(1), 200-206.

Murali et al., "Antibody Like Peptidomimetics as Large Scale Immunodetection Probes", Cell. Mol. Biol., Mar. 2003, 49(2), 209-216.

Murali et al., "Structural analysis of p185(c-neu) and epidermal growth factor receptor tyrosine kinases: Oligomerization of kinase domains", Proc. Natl. Acad. Sci. USA, Jun. 25, 1996, 93(13), 6252-6257.

Murali et al., "Structure-based design of immunologically active therapeutic peptides", Immunol. Res., Jan. 1998, 17(1-2), 163-169.

Murzin et al., "SCOP: A Structural Classification of Proteins Database for the Investigation of Sequences and Structures", J. Mol. Biol., Apr. 1995, 247, 536-540.

Muyldermans et al., "Unique Single-Domain Antigen Binding Fragments Derived From Naturally Occurring Camel Heavy-Chain Antibodies", J. of Molecular Recognition, Mar. 1999, 12(2), 131-140.

Myers et al., "PTEN: sometimes taking it off can be better than putting it on", Am. J. Hum. Genet., Dec. 1997, 61(6), 1234-1238.

Myers et al., "The lipid phosphatase activity of PTEN is critical for its tumor supressor function", Proc. Natl. Acad. Sci. USA, Nov. 10, 1998, 95(23), 13513-13518.

Nagane et al., "A common mutant epidermal growth factor receptor confers enhanced tumorigenicity on human glioblastoma cells by increasing proliferation and reducing apoptosis", Cancer Research, Nov. 1, 1996, 56(21), 5079-5086.

Nagane et al., "Drug resistance of human glioblastoma cells conferred by a tumor- specific mutant epidermal growth factor receptor through modulation of Bcl-XL and caspase-3-like proteases", Proc. Natl. Acad. Sci. USA, May 12, 1998, 95(10), 5724-5729.

Nagata et al., "The Fas death factor", Science, Mar. 1995, 267(5203), 1449-1456.

Naismith et al., "Crystallographic Evidence For Dimerization of Unliganded Tumor Necrosis Factor Receptor", J. of Biological Chemistry, Jan. 2, 1995, 270(22), 13303-13307.

Naismith et al., "Crystallographic Evidence For Dimerization of Unliganded Tumor Necrosis Factor Receptor", J. Biol. Chem., Jun. 1995, 270, 13303-13307.

Naismith et al., "Modularity in the TNF-Receptor Family", Trends in Biochemical Sciences, Feb. 1998, 23(2), 74-79.

Naismith et al., Structures of the extracellular domain of the type I tumor necrosis factor receptor, Structure, Nov. 1996, 4(11), 1251-1262.

Nayak et al., "B Cell Responses To A Peptide Epitope. V. Kinetic Regulation of Repertoire Discrimination and Antibody Optimization For Epitope", J. of Immunology, Oct. 1998, 161(7), 3510-3519.

Neuberger et al., "Recombinant antibodies possessing novel effector functions", Nature, Dec. 1984, 312, 604-608.

Nishikawa et al., "A mutant epidermal growth factor receptor common in human glioma confers enhanced tumorigenicity", Proc. Natl. Acad. Sci. USA, Aug. 2, 1994, 91(16), 7727-7731.

OConnell et al., "The Fas counterattack: a molecular mechanism of tumor immune privilege", Molecular Medicine, May 1997, 3(5), 294-300.

Ohno et al., "Cell-specific, multidrug delivery system using streptavidin-protein A fusion protein," Biochem. Mol. Med., Aug. 1996, 58(2), 227-233.

Ohno et al., "Multi-drug delivery system using streptavidin-transforming growth factor alpha chimeric protein," DNA Cell Biol., May 1996, 15(5), 401-406.

Okada et al., "Differential effects of cytotoxic drugs on mortal and immortalized B-lymphoblastoid cell lines from normal and Werner's syndrome patients", Biol. Pharm. Bull., Mar. 1998, 21(3), 235-239.

Okuda et al., "Intrathecal Administration of Neutralizing Antibody against Fas Ligand Suppresses the Progression of Experimental Autoimmune Encephalomyelitis," Biochem. Biophys. Res. Commun., Aug. 2000, 275(1), 164-168.

O'Rourke et al., "Inhibition of a Naturally Occurring EGFR Oncoprotein by the p185neu Ectodomain: Implications for Subdomain Contributions to Receptor Assembly," Oncogene, Mar. 5, 1998, 16(9), 1197-1207.

O'Rourke et al., "Conversion of a radioresistant phenotype to a more sensitive one by disabling erbB receptor signaling in human cancer cells", Proc. Natl. Acad. Sci. USA, Sep. 1, 1998, 95(18), 10842-10847.

O'Rourke et al., "Trans Receptor Inhibition of Human Glioblastoma Cells by erbB Family Ectodomains", Proc. Natl. Acad. Sci. USA, Apr. 1, 1997, 94(7), 3250-3255.

Pages et al., "sst2 somatostatin receptor mediates cell cycle arrest and induction of p27(Kip1). Evidence for the role of SHP-1", J. Biol. Chem., May 21, 1999, 274(21), 15186-15193.

Panicali et al., "Construction of poxviruses as cloning vectors: insertion of the thymidine kinase gene from herpes simplex virus into the DNA of infectious vaccinia virus", PNAS, Aug. 1982, 79(16), 4927-4931.

Park et al., Induction of the Tat-binding protein 1 gene accompanies the disabling of oncogenic erbB receptor tyrosine kinases. Proc. Nat. Acad. Sci. USA, May 25, 1999, 96(11), 6434-6438.

Park, "Rationally Designed Anti-HER2/neu Peptide Mimetic Disables P185HER2/neu Tyrosine Kinases in Vitro and in Vivo," Nat. Biotechnology, Feb. 2000, 18(2), 194-198.

(56) References Cited

OTHER PUBLICATIONS

Patel et al., "A Cyclic Peptide Analogue of the Loop III Region of Platelet-derived Growth Factor-BB Is A Synthetic Antigen For the Native Protein", J. of Peptide Research, Jan. 1999, 53(1), 68-74.

Pearce, et al. "Linear gene fusions of antibody fragments with streptavidin can be linked to biotin labelled secondary molecules to form bispecific reagents," Biochem. Mol. Biol. Int., Sep. 1997, 42(6), 1179-1188.

Peczuh et al., "Peptide and Protein Recognition by Designed Molecules", Chem. Rev., Jul. 2000, 100, 2479-2494.

Pegram et al., "Phase II Study of Receptor-Enhanced Chemosensitivity Using Recombinant Humanized Anti-p185HER2/neu Monoclonal Antibody Plus Cisplatin in Patients With HER2/neu-overexpressing Metastatic Breast Cancer Refractory To Chemotherapy Treatment", J. of Clinical Oncology, Aug. 1998, 16(8), 2659-2671.

Peterson et al., "Bacterial Expression and Characterization of Recombinant Biologically-Active Anti-Tyrosine Kinase Receptor Antibody-Forms", DNA Cell Biology, Dec. 1998, 17(12), 1031-1040.

Pianetti et al., "Her-2/neu overexpression induces NF-kappaB via a PI3-kinase/Akt pathway involving calpain-mediated degradation of IkappaB-alpha that can be inhibited by the tumor suppressor PTEN", Oncogene, Mar. 15, 2001, 20(11), 1287-1299.

Pinkas-Kramarski et al., "Differential Expression of NDF/Neuregulin Receptors ErbB-3 andErbB-4 and Involvement In Inhibition of Neuronal Differentiation", Oncogene, Dec. 4, 1997, 15(23), 2803-2815.

Pinkas-Kramarski et al., "Diversification of Neu differentiation factor and epidermal growth factor signaling by combinatorial receptor interactions", EMBO J., May 15, 1996, 15(10), 2452-2467.

Ploux et al., "Cyclization of peptides on a solid support. Application to cyclic analogs of substance P," Int. J. Pep. Prot. Res., Feb. 1987, 29, 162-169.

Ponder et al., "Tertiary templates for proteins. Use of packing criteria in the enumeration of allowed sequences for different structural classes", J. Mol. Biol., Feb. 1987, 193, 775-791.

Porstmann et al., "Enzyme immunoassay techniques. An overview," J Immunol. Methods, Jun. 1992, 150(1-2), 5-21.

Porstmann et al., "Which of the commonly used marker enzymes gives the best results in colorimetric and fluorimetric enzyme immunoassays: horseradish peroxidase, alkaline phosphatase or beta-galactosidase?" J Immunol. Methods, May 1985, 79(1), 27-37.

Posthumus et al., "Immunogenicity of Peptides Simulating A Neutralization Epitope of Transmissible Gastroenteritis Virus", Virology, May 1991, 182(1), 371-375.

Prasad et al., "Contrasting solution conformations of peptides containing alpha,alpha-dialkylated residues with linear and cyclic side chains," Biopolymers, Jan. 1995, 35, 11-20.

Qian et al., "Domain-specific interactions between the p185 neu and EGF receptor kinases determine differential signalling outcomes", J. of Biological Chemistry, Jan. 8, 1999, 274(12), 574-583.

Qian et al., "Heterodimerization of Epidermal Growth Factor Receptor and Wild-Type of Kinase-Deficient Neu: A Mechanism of Inter-receptor Kinase activation and Transphosphorylation", Proc. Natl. Acad. Sci. USA, Feb. 15, 1994, 91(4), 1500-1504.

Qian et al., "Identification of p185 sequences required for monoclonal antibody- or ligand-mediated receptor signal attenuation", DNA Cell Biology, Dec. 1997, 16(12), 1395-1405.

Qian et al., "Inhibition of p185neu kinase activity and cellular transformation by co-expression of a truncated neu protein", Oncogene, Nov. 21, 1996, 13(10), 2149-2157.

Qian et al., "Intermolecular association and trans-phosphorylation of different neu- kinase forms permit SH2-dependent signaling and oncogenic transformation", Oncogene, Jan. 5, 1995, 10(1), 211-219.

Qian et al., "Kinase-deficient neu proteins suppress epidermal growth factor receptor function and abolish cell transformation", Oncogene, May 1994, 9(5), 1507-1514.

Ramachandran et al., "Stereochemical criteria for polypeptides and proteins. IV. Standard dimensions for the cis-peptide unit and conformation of cis-polypeptides", Biopolymers, Sep. 1968, 6(9), 1255-1262.

Ramachandran et al., "Conformation of Polypeptides and Proteins," Adv. Protein Chem., 1968, 23, 283-438.

Reichmann, "Rearrangement of the Former VL Interface in the Solution Structure of a Camelised, Single Antibody VH Domain", J. of Molecular Biology, Jun. 28, 1996, 259(5), 957-969.

Riese et al., "Activation of ErbB4 by the bifunctional epidermal growth factor family hormone epiregulin is regulated by ErbB2", J. Biol. Chem., May 1, 1998, 273(18), 11288-11294.

Riethmacher et al., "Severe neuropathies in mice with targeted mutations in the ErbB3 receptor", Nature, Oct. 16, 1997, 389(6652), 725-730.

Rizzo et al., "Ontogeny of Microvascular Permeability to Macromolecules in the Chick Chorioallantoic Membrane during Normal Angiogenesis", Microvasc. Res., Jan. 1995, 49, 49-63.

Rogers et al., "Characterization of disulfide crosslink formation of human vimentin at the dimer, tetramer, and intermediate filament levels," Struct. Biol., Jul./Aug. 1996, 117(1), 55-69.

Roland et al., "The synthetic CD4 exocyclic CDR3.AME(82-89) inhibits NF-kappaB nuclear translocation, HIV-1 promoter activation, and viral gene expression," DNA Cell Biol., Nov. 1999, 18(11), 819-828.

Romani et al., "Synthesis of the trypsin fragment 10-25/75-88 of mouse nerve growth factor. II. The unsymmetrical double chain cystine peptide", Int. Pep. Prot. Res., Jan. 1987, 29, 107-117.

Rudikoff et al., "Single amino acid substitution altering antigen-binding specificity" PNAS, Mar. 1982, 79, 1979.

Sali et al., "From comparisons of protein sequences and structures to protein modelling and design", Trends in Biochem. Sci., Jun. 1990, 15, 235-240.

Sali et al., "Definition of general topological equivalence in protein structures: A procedure involving comparison of properties and relationships through simulated annealing and dynamic programming," J. Mol. Biol., Mar. 1990, 212(2), 403-428.

Samanta et al., "Quantifying the accessible surface area of protein residues in their local environment", Prot. Eng., Aug. 2002, 15(8), 659-667.

Samata et al, "Ligand and p185 density govern receptor interactions and tyrosine kinase activation", PNAS, Mar. 1994, 91, 1711.

Sano and Cantor, "Expression of a cloned streptavidin gene in *Escherichia coli*," Proc. Natl. Acad. Sci.,Jan. 1990, 87(1), 142-146.

Sano and Cantor, "Expression vectors for streptavidin-containing chimeric proteins," Biochem. Biophys. Res. Commun., Apr. 1991, 176(2), 571-577.

Sano et al., "A streptavidin-metallothionein chimera that allows specific labeling of biological materials with many different heavy metal ions," Proc. Natl. Acad. Sci., Mar. 1992, 89(5), 1534-1538.

Sano et al., "A streptavidin-protein A chimera that allows one-step production of a variety of specific antibody conjugates", Biotechnology, Dec. 1991, 1378-1381.

Saragovi et al., "Constrained peptides and mimetics as probes of protein secondary structures", Immunomethods, Aug. 1992, 1(1), 5-9.

Saragovi et al., "Design and Synthesis of a Mimetic from an Antibody Complementarity-Determining Region", Science, Aug. 1991, 253, 792-795.

Saxon et al., "Mutagenesis Reveals a Role For Epidermal Growth Factor Receptor Extracellular Subdomain IV In Ligand Binding", J. of Biological Chemistry, Oct. 1, 1999, 274(40), 28356-28362.

Saxton et al., "Abnormal mesoderm patterning in mouse embryos mutant for the SH2 tyrosine phosphatase Shp-2", EMBO J., May 1, 1997, 16(9), 2352-2364.

Schechter et al., "The neu oncogene: an erb-B-related gene encoding a 185,000-Mr tumour antigen", Nature, Dec. 6-12, 1984, 312(5994), 513-516.

Schiller et al., "Synthesis of side-chain to side-chain cyclized peptide analogs on solid supports", Int. Pep. Prot. Res., Feb. 1985, 25(2), 171-177.

(56) References Cited

OTHER PUBLICATIONS

Schmidt et al., "Targeted inhibition of tumour cell growth by a bispecific single-chain toxin containing an antibody domain and TGF alpha", Brit. J. Cancer, Sep. 1996, 74(6), 853-862.
Schweitzer et al., "Inaugural article: immunoassays with rolling circle DNA amplification: a versatile platform for ultrasensitive antigen detection," Proc Natl. Acad Sci., Aug. 2000, 97(18),10113-10119.
Scott et al, "p185 signal transduction in breast cancer cells", J. Biochemistry, Aug. 1991, 266(22), 14300-14305.
Seino et al., "Contribution of Fas ligand to T cell-mediated hepatic injury in mice", Gastroenterology, Oct. 1997, 113(4), 1315-1322.
Seino et al., "Cutting Edge: Chemotactic Activity of Soluble Fas Ligand Against Phagocytes", J. Immunol., Nov. 1998, 161(9), 4484-4488.
Sharov et al., "Fas Signaling Is Involved in the Control of Hair Follicle Response to 6-7 Chemotherapy," Cancer Res., Sep. 1, 2004, 64, 6266-6270.
Shayesteh et al., "PIK3CA is implicated as an oncogene in ovarian cancer", Nat. Genet., Jan. 1999, 21(1), 99-102.
Sheppard, "Acid-labile resin linkage agents for use in solid phase peptide synthesis", Intl. Peptide Prot. Res., Nov. 1982, 20(5), 451-454.
Shi et al., "Molecular mechanism for the Shp-2 tyrosine phosphatase function in promoting growth factor stimulation of Erk activity", Molecular and Cellular Biology, Mar. 2000, 20(5), 1526-1536.
Shi et al., "The Shp-2 tyrosine phosphatase has opposite effects in mediating the activation of extracellular signal-regulated and c-Jun NH2-terminal mitogen-activated protein kinases", J. Biol. Chem., Feb. 27, 1998, 273(9), 4904-4908.
Simonovic et al., "Crystal structure of human PEDF, a potent anti-angiogenic and neurite growth-promoting factor", PNAS, Sep. 2001, 98, 11131-11135.
Simpson et al., "Influence of Location and Extent of Surgical Resection on Survival of Patients with Glioblastoma Multiforme: Results of Three Consecutive Radiation Therapy Oncology Group {RTOG} Clinical Trials", Int. J. Radial. Oncol. Biol. Phys., May 1993, 26, 239-244.
Smith et al., "Molecular Engineering of the Autographa californica Nuclear Polyhedrosis Virus Genome: Deletion Mutations Within the Polyhedrin Gene", J. Virol., May 1983, 46(2), 584-593.
Song et al., "RNA interference targeting Fas protects mice from fulminant hepatitis," Nat. Med., Mar. 2003, 9(3), 347-351.
Srinivasan et al., "Immunomodulatory peptides from IgSF proteins: a review", Curr. Protein Pept. Sci., Apr. 2005, 6(2), 185-196.
Stambolic et al., "Negative regulation of PKB/Akt-dependent cell survival by the tumor suppressor PTEN", Cell, Oct. 2, 1998, 95(1), 29-39.
Starling et al., Identification of Amino Acid Residues Important for Ligand Binding to Fas, J. Exp. Med., Apr. 1997, 185, 1487-1492.
Steck et al., "Identification of a candidate tumour suppressor gene, MMAC1, at chromosome 10q23.3 that is mutated in multiple advanced cancers", Nat. Genet., Apr. 1997, 15(4), 356-362.
Stellmach et al., "Prevention of ischemia-induced retinopathy by the natural ocular antiangiogenic agent pigment epithelium-derived factor", PNAS, Feb. 2001, 98(5), 2593-2597.
Stryer et al., "Biochemistry," Third edition, W H Freeman Company, New York, pp. 31-33, 1998.
Stuart et al., "CD95 ligand (FasL)-induced apoptosis is necessary for corneal allograft survival", J. Clin. Invest., Feb. 1997, 99(3), 396-402.
Stuart et al., "FasL-Fas Interactions Regulate Neovascularization in the Cornea", Invest. Ophthalmol. Vis. Sci., Jan. 2003, 44(1), 93-98.
Suda et al., "Expression of the Fas ligand in cells of T cell lineage", J. Immunol., Apr. 1995, 154, 3806-3813.
Suda et al., "Molecular cloning and expression of the Fas ligand, a novel member of the tumor necrosis factor family", Cell, Dec. 1993, 75(6), 1169-1178.
Summerfield et al., "Identification of Residues of the Epidermal Growth Factor Receptor Proximal To Residue 45 of Bound Epidermal Growth Factor", J. of Biological Chemistry, Aug. 16, 1996, 271(33), 19656-19659.
Sun et al., "Cell death mediated by Fas-FasL interaction between glial cells and MBP-reactive T cells", J. Neurosci. Res., May 15, 1998, 52(4), 458-467.
Tagawa et al, "Involvement of Fas/Fas ligand system-mediated apoptosis in the development of concanavalin A-induced hepatitis", Eur. J. Immunol., Dec. 1998, 28(12), 4105-4113.
Tagawa et al., "Suppression of concanavalin A-induced hepatitis in IFN-gamma(−/−) mice, but not in TNF-alpha(−/−) mice: role for IFN-gamma in activating apoptosis of hepatocytes", J. Immunol., Aug. 1997, 159(3), 1418-1428.
Tahna et al. "Optimal Design Features of Camelized Human Single-Domain Antibody Libraries", J. of Biological Chemistry, Jul. 6, 2001, 276(27), 24774-24780.
Takada et al., "Roles of the complex formation of SHPS-1 with SHP-2 in insulin- stimulated mitogen-activated protein kinase activation", J. Biol. Chem., Apr. 10, 1998, 273(15), 9234-9242.
Takamatsu et al., "Expression of bacterial chloramphenicol acetyltransferase gene in tobacco plants mediated by TMV-RNA", EMBO J., Feb. 1987, 6, 307-311.
Takasaki et al., "Structure-Based Design and Characterization of Exocyclic Peptidomimetics That Inhibit TNF Alpha Binding To Its Receptor", Nature Biotechnology, Nov. 1997, 15(12), 1266-1270.
Takeda et al., "Construction of chimaeric processed immunoglobulin genes containing mouse variable and human constant", Nature, Apr. 1985, 314, 452-454.
Tam et al. "Improved Synthesis of 4-(Boc-aminoacyloxymethyl)-phenylacetic Acids for use in Solid Phase Peptide Synthesis", Synthesis, Dec. 1979, 955-957.
Tamura et al., "Inhibition of cell migration, spreading, and focal adhesions by tumor suppressor PTEN", Science, Jun. 5, 1998, 280(5369), 1614-1617.
Taniwaki et al., "Pigment Epithelium-Derived Factor Protects Cultured Cerebellar Granule Cells Against Glutamate-Induced Neurotoxicity", J. Neurochem., Jan. 1997, 68(1), 26-32.
Tannous et al., "T7 RNA polymerase as a self-replicating label for antigen quantification", Nucleic Acids Res., Dec. 2002, 30(24), 140.
Tejero et al., "Simulated Annealing With Restrained Molecular Dynamics Using CONGEN: Energy Refinement of the NMR Solution Structures of Epidermal and Type-α Transforming Growth Factors", Protein Science, Apr. 1996, 5(4), 578-592.
Testa, B., "Prodrug research: futile or fertile?," Biochemical Pharmacology, Dec. 1, 2004, 68(11), 2097-2106.
Tiedeken et al., "Fluorescent imaging in vivo of developing blood vessels on the optic tectum of *Xenopus laevis*", Microvasc. Res., May 1991, 41, 376-389.
Tiegs et al., "A T cell-dependent experimental liver injury in mice inducible by concanavalin A", J. Clin. Invest., Jul. 1992, 90, 196-203.
Tombran-Tink et al., "Expression, secretion, and age-related downregulation of pigment epithelium-derived factor, a serpin with neurotrophic activity", J. Neurosci., Jul. 1995, 15, 4992-5003.
Tonks et al., "Structural assets of a tumor suppressor", Science, Dec. 10, 1999, 286(5447), 2096-2097.
Toyabe et al., "Requirement of IL-4 and liver NK1+ T cells for concanavalin A-induced hepatic injury in mice", J. Immunol., Aug. 1997, 159(3), 1537-1542.
Tzahar et al., Bivalence of EGF-Like Ligands Drives the ErbB Signaling Network, EMBO J., Aug. 15, 1997, 16(16), 4938-4950.
Tzahar et al., "The ErbB-2/HER2 oncogenic receptor of adenocarcinomas: from orphanhood to multiple stromal ligands", Biochim. Biophys. Acta., Feb. 20, 1998, 1377(1), M25-M37.
Ullrich et al., "Human Epidermal Growth Factor Receptor cDNA Sequence and Aberrant Expression of the Amplified Gene in A431 Epidermoid. Carcinoma Cells", Nature, May 31, 1984, 309(5967), 418-425.
Valero et al., "Cyclic peptides as conformationally restricted models of viral antigens: application to foot-and-mouth disease virus", Biomed. Pept. Proteins Nucleic Acids, Apr. 1995, 1(3), 133-140.

(56) References Cited

OTHER PUBLICATIONS

Van Regenmortel, M., "Mapping Epitope Structure and Activity: From One-Dimensional Prediction to Four-Dimensional Description of Antigenic Specificity", Methods, Jun. 1996, 9(3), 465-472.

Van Regenmortel, M., "Structural and Functional Approaches to the Study of Protein Antigenicity", Immunology Today, Aug. 1989, 10(18), 266-272.
Vanderwerf et al., "Ability of linear and cyclic peptides of neutralization antigenic site 1 of poliovirus type 1 to induce virus cross-reactive and neutralizing antibodies", Res Virol, Nov./Dec. 1994, 145, 349-359.
Veillette et al., "High expression of inhibitory receptor SHPS-1 and its association with protein-tyrosine phosphatase SHP-1 in macrophages", J. Biol. Chem., Aug. 28, 1998, 273(35), 22719-22728.
Vita et al., "Novel Miniproteins Engineered By the Transfer of Active Sites to Small Natural Scaffolds", Biopolymers Peptide Science, Dec. 6, 1998, 47(1), 93-100.
Vogelstein et al., "Surfing the p53 network", Nature, Nov. 16, 2000, 408(6810), 307-310.
Voice et al., "Four human ras homologs differ in their abilities to activate Raf-1, induce transformation, and stimulate cell motility", J. Biol. Chem., Jun. 11, 1999, 274(24), 17164-17170.
Volpert et al., "Inducer-stimulated Fas targets activated endothelium for destruction by anti-angiogenic thrombospondin-1 and pigment epithelium-derived factor", Nature Medicine, Apr. 2002, 8(4), 349-357.
Wada et al., "Anti-receptor antibodies reverse the phenotype of the cells transformed by two interacting proto-oncogene encoded receptor proteins", Oncogene, Apr. 1990, 5(4), 489-495.
Wada et al., "Intermolecular Association of the P185Neu Protein and EGF Receptor Modulates EGF Receptor Function", Cell, Jun. 29, 1990, 61(7), 1339-1347.
Waid et al., "Constrained Amino Acids: An Approach to the Synthesis of 3-Substituted Prolines", Tetrahedron Letters, Jun. 10, 1996, 37(24), 4091-4094.
Walsh et al., "An *Escherichia coli* plasmid vector system for production of streptavidin fusion proteins: expression and bioselective adsorption of streptavidin-beta-galactosidase," Biotech. Bioeng., Dec. 1994, 44, 1348-1354.
Wang et al., ErbB2 Expression Increases the Spectrum and Potency of Ligand-Mediated Signal Transduction Through ErbB4, Proc. Natl. Acad. Sci. USA, Jun. 9, 1998, 95(12), 6809-6814.
Ward et al., "Insulin and Epidermal Growth Factor Receptors Contain the Cysteine Repeat Motif Found In the Tumor Necrosis Factor Receptor", Proteins, Jun. 1995, 22(2), 141-153.
Watanabe et al., "Concanavalin A induces perforin-mediated but not Fas-mediated hepatic injury", Hepatology, Sep. 1996, 24(3), 702-710.
Watanabe-Fukunaga et al., "The cDNA structure, expression, and chromosomal assignment of the mouse Fas antigen", J. Immunol., Feb. 1992, 148(4), 1274-1279.
Wigginton et al., "IFN-γ and Fas/FasL are required for the antitumor and antiangiogenic effects of IL-12/pulse IL-2 therapy", J. Clin. Invest., Jul. 2001, 108(1), 51-62.
Williams et al., "Immune Response To a Molecularly Defined Internal Image Idiotope", J. of Immunology, Jun. 15, 1989, 142(12), 4392-4400.
Williams et al.,"Development of biologically active peptides based on antibody structure", Proc. Natl Acad. Sci., Jul. 1989, 86, 5537-5541.
Witte et al., "Monoclonal antibodies targeting the VEGF receptor-2 (flk1/KDR) as an anti-angiogenic therapeutic strategy", Cancer and Metastasis Reviews, 1998, 17, 155-161.
Woltjer et al., "Direct Identification of Residues of the Epidermal Growth Factor Receptor In Close Proximity to the Amino Terminus of Bound Epidermal Growth Factor", Proc. Natl. Acad. Sci. USA, Sep. 1, 1992, 89(17), 7801-7805.
Wong et al., "Structural alterations of the epidermal growth factor receptor gene in human gliomas", Proc. Natl. Acad. Sci. USA, Apr. 1992, 89(7), 2965-2969.
Wood et al., "Novel cyclization chemistry especially suited for biologically derived, unprotected peptides", J. Pep. Prot. Res., Jun. 1992, 39, 533-539.
Worthylake et al., "ErbB-2 amplification inhibits down-regulation and induces constitutive activation of both ErbB-2 and epidermal growth factor receptors", J. Biol. Chem., Mar. 26, 1999, 274(13), 8865-8874.
Wrighton et al. "Increased potency of an erythropoietin peptide mimetic through covalent dimerization", Nat. Biotechnol., Nov. 1997, 15, 1261-1265.
Wu et al., "Inhibition of EGFR-mediated phosphoinositide-3-OH kinase (PI3-K) signaling and glioblastoma phenotype by Signal-Regulatory Proteins (SIRPs)", Oncogene, Aug. 17, 2000, 19(35), 3999-4010.
Wu et al., "The PTEN/MMAC1 tumor suppressor phosphatase functions as a negative regulator of the phosphoinositide 3-kinase/Akt pathway", Proc. Natl. Acad. Sci. USA, Dec. 22, 1998, 95(26), 15587-15591.
Yamauchi et al., "Epidermal growth factor-induced association of the SHPTP2 protein tyrosine phosphatase with a 115-kDa phosphotyrosine protein", J. Biol. Chem., Jun. 23, 1995, 270(25), 14871-14874.
Yamauchi et al., "Introduction of a Foreign Gene Into Medakafish Using the Particle Gun Method", J. of Experimental Zoology, Jun. 23, 2000, 287(25), 285-293.
Ye et al., "Augmentation of a humanized anti-HER2 mAb 4D5 induced growth inhibition by a human-mouse chimeric anti-EGF receptor mAb C225", Oncogene, Jan. 21, 1999, 18(3), 731-738.
Yiallouros et al., "Phosphinic peptides, the first potent inhibitors of astacin, behave as extremely slow-binding inhibitors", Biochem. J., Apr. 1998, 331, 375-379.
Yip et al, "Identification of epitope regions recognized by tumor inhibitory and stimulatory anti-erbB-2 monoclonal antibodies: implication for cavvine design", J. Immunology, Apr. 2001, 166, 5271-5278.
Zajchowski et al., "Identification of Gene Expression Profiles That Predict the Aggressive behavior of Breast Cancer Cells", Cancer Res., Jul. 2001, 61, 5168-5178.
Zhang et al., "Absence of autophosphorylation site Y882 in the p185neu oncogene product correlates with a reduction of transforming potential", Oncogene, Jun. 4, 1998, 16(22), 2835-2842.
Zhang et al., "Crystal structure of recombinant human platelet factor 4", Biochem., Nov. 1994, 33(27), 8361-8366.
Zhang et al., "New Perspectives on Anti-HER2/Neu Therapeutics", Drug News Perspect., Aug. 2000, 13(6), 325-329.
Zhang et al., "Protein Quantification from Complex Protein Mixtures Using a Novel Proteomics Methodology with Single Cell Resolution", Proc. Natl. Acad. Sci. USA, May 8, 2001, 98(10), 5497-5502.
Zhang et al., "Shared antigenic epitopes and pathobiological functions of anti-p185her2/neu monoclonal antibodies", Experimental and Molecular Pathology, Sep. 1999, 67(1), 15-25.
Zhang et al., "Synthetic CD4 Exocyclic Peptides Antagonize CD4 Holoreceptor Binding and T-Cell Activation", Nature Biotechnology, Apr. 1996, 14(4), 472-475.
Zhang et al., "Synthetic CD4 Exocyclics Inhibit Binding of Human Immunodeficiency Virus Type 1 Envelope to CD4 and Virus Replication in T Lymphocytes", Nature Biotechnology, Feb. 1997, 15(2), 150-154.
Zhang et al., "The three-dimensional profile method using residue preference as a continuous function of residue environment", Protein Sci., Apr. 1994, 3(4), 687-695.
Zhang et al., "VCP, a Weak ATPase Involved In Multiple Cellular Events, Interacts Physically With BRCA1 In the Nucleus of Living Cells", DNA and Cell Biology, May 2000, 19(5), 253-263.
Zhang et al.,"Reduction of liver Fas expression by an antisense oligonucleotide protects mice from fulminant hepatitis", Nat. Biotechnol., Aug. 2000, 18(8), 862-867.
Zuckermann, "The Chemical Synthesis of Peptidomimetic Libraries", Current Opinion in Structural Biology, Aug. 1993, 3(4), 580-584.
Zutshi et al., "Inhibiting the Assembly of Protein-Protein Interfaces", Current Opinion in Chemical Biology, Feb. 1998, 2(1), 62-66.

FIG. 1A
FIG. 1B
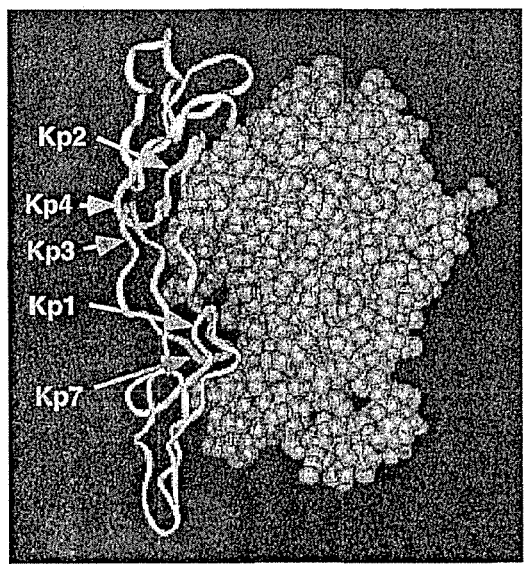 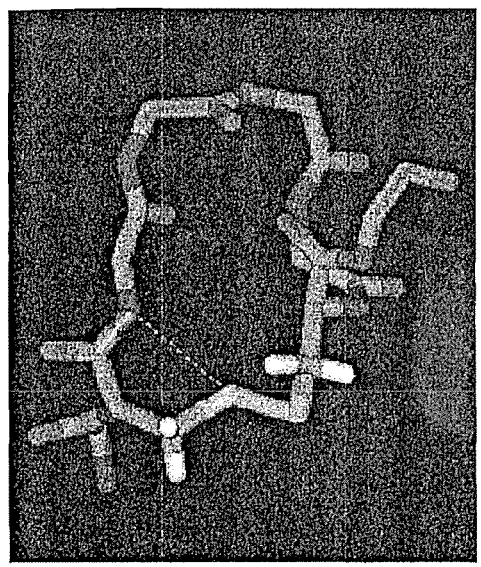

FAS PEPTIDE MIMETICS AND USES THEREOF

CROSS-REFERENCE TO RELATED APPLICATIONS

This application is a divisional of U.S. application Ser. No. 11/869,556 filed on Oct. 9, 2007, now allowed, which is a continuation of U.S. application Ser. No. 10/445,399, filed May 23, 2003, now U.S. Pat. No 7,288,519 which in turn claimed priority under 35 U.S.C. §119 (e) to U.S. Provisional Application Ser. No. 60/383,309, filed May 23, 2002, and 60/465,943, filed Apr. 28, 2003 all of which are incorporated herein by reference and in their entireties.

GOVERNMENT SUPPORT

The work leading to this invention was supported at least in part by grants PO1 CA89480 and RO1 89481 awarded by the National Cancer Institute. The United States government may have certain rights to this invention pursuant to the terms of those grants.

FIELD OF THE INVENTION

The present invention relates to therapeutic agents that act by disrupting or inhibiting signaling through cell surface receptors. More specifically, the invention is directed to peptide mimetics that inhibit signaling through the Fas receptor, and to methods of using such peptide mimetics to treat Fas-related pathologies.

BACKGROUND OF THE INVENTION

Fas (CD95/APO-1) and its specific ligand (FasL/CD95L) are members of the tumor necrosis factor (TNF) receptor and TNF families of proteins, respectively. (Nagata, S. et al. *Science* 267, 1449-1456 (1995). Interaction between Fas and FasL triggers a cascade of subcellular events that results in a definable cell death process in Fas-expressing targets. Fas is a 45 kDa type I membrane protein expressed constitutively in various tissues, including spleen, lymph nodes, liver, lung, kidney and ovary. (Leithauser, F. et al. *Lab Invest* 69, 415-429 (1993); Watanabe-Fukunaga, R. et al. *J Immunol* 148, 1274-1279 (1992)). FasL is a 40 kDa type II membrane protein, and its expression is predominantly restricted to lymphoid organs and perhaps certain immune-privileged tissues. (Suda, T. et al. *Cell* 75, 1169-1178 (1993); Suda, T. et al. *J Immunol* 154, 3806-3813 (1995)). In humans, FasL can induce cytolysis of Fas-expressing cells, either as a membrane-bound form or as a 17 kDa soluble form, which is released through metalloproteinase-mediated proteolytic shedding. (Kayagaki, N. et al. *J Exp Med* 182, 1777-1783 (1995); Mariani, S. M. et al. *Eur J Immunol* 25, 2303-2307 (1995)).

The FasL/Fas system has been implicated in the control of the immune response and inflammation, the response to infection, neoplasia, and death of parenchymal cells in several organs. (Nagata et al. supra; Biancone, L. et al. *J Exp Med* 186, 147-152 (1997); Krammer, P. H. *Adv Immunol* 71, 163-210 (1999); Seino, K. et al. *J Immunol* 161, 4484-4488 (1998)). Defects of the FasL/Fas system can limit lymphocyte apoptosis and lead to lymphoproliferation and autoimmunity. A role for FasL-Fas in the pathogenesis of rheumatoid arthritis, Sjogren's syndrome, multiple sclerosis, viral hepatitis, renal injury, inflammation, aging, graft rejection, HIV infection and a host of other diseases has been proposed. (Famularo, G., et al. *Med Hypotheses* 53, 50-62 (1999)). Fas mediated apoptosis is an important component of tissue specific organ damage, such as liver injury which has been shown to be induced through the engagement of the Fas-FasL receptor system. (Kakinuma, C. et al. *Toxicol Pathol* 27, 412-420 (1999); Famularo et al. supra; Martinez, O. M. et al. *Int Rev Immunol* 18, 527-546 (1999); Kataoka, Y. et al. *Immunology* 103, 310-318 (2001); Chung, C. S. et al. *Surgery* 130, 339-345 (2001); Doughty, L. et al. *Pediatr Res* 52, 922-927 (2002)). Consequently, the FasL-Fas pathway represents an important general target for therapeutic intervention.

Monoclonal anti-FasL antibody and recombinant soluble Fas protein are well recognized potential candidate antagonists for clinical studies. (Hashimoto, H. et al. *Arthritis and Rheumatism* 41, 657-662 (1998); Kanda, Y. et al. *Bone Marrow Transplantation* 22, 751-754 (1998); Kato, K. et al. *British Journal of Haematology* 103, 1164-1166 (1998); Maggi, C. A. *Pharmacological Research* 38, 1-34 (1998)). Attempts to neutralize FasL with antibodies has been examined in a variety of animal models. (Okuda, Y. et al. *Biochem Biophys Res Commun* 275, 164-168 (2000)). While antibodies have a long half life and are highly specific they also have important limitations: (i) commercial-scale production may be either difficult or costly, (ii) conformational stability may vary with the environment of the body fluids, (iii) antibodies may be excluded from certain compartments e.g., the brain, due to failure to cross the blood/brain barrier, and (iv) they may lead to the development of neutralizing antibodies, etc. (Cho, M. J. et al. *Trends Biotechnol* 14, 153-158 (1996)).

Many disadvantages of large macromolecules can be overcome by creating small molecular inhibitors that are targeted to surface receptors or their ligands. Peptidomimetics that are constructed to resemble secondary structural features of the targeted protein represent an approach to overcome some of the limitations of macromolecules and can mimic inhibitory features of large molecules such as antibody (Park, B. W. et al. *Nat Biotechnol* 18, 194-198 (2000)) and soluble receptors. (Takasaki, W. et al. *Nat Biotechnol* 15, 1266-1270 (1997)). Recently several peptidomimetics that inhibit ligand-receptor binding and that mediate potent biological effects have been described. (Park et al. supra; Takasaki, et al. supra). These peptides represent novel small molecular tools that can act with potency comparable to or equivalent to the natural antagonist. (Takasaki et al. supra; Wrighton, N. C. et al. *Nat Biotechnol* 15, 1261-1265 (1997)).

Several studies suggest that the presence of FasL in the eye is a barrier to both inflammatory cells (Griffith, T. S., et al., *Science*, 270, 1189-92 (1995); Gao, Y., et al., *J Exp Med.*, 188, 887-96, (1998)) and development of new blood vessels (Kaplan, H. J., et al., *Nat. Med.*, 5, 292-97 (1999)). The control of inflammation is known to be a component of the immune privilege of the eye (Griffith et al., 1995, supra; Griffith, T. S., et al., *Immunity*, 5, 7-16 (1996); Greil, R., A., et al., *Leukemia & Lymphoma*, 31, 477, (1998); Oconnell, J., et al., *Molecular Medicine*, 3, 294-300 (1997)). FasL expression in ocular tissue induces apoptosis in Fas$^+$ lymphoid cells that invade the eye in response to viral infection or corneal grafting (Griffith, T. S., et al., 1995, supra; Stuart, P. M., et al., *J Clin Invest*, 99, 396-402 (1997); Chen, J. J., et al., *Science*, 282, 1714-1717 (1998); Mohan, R. R., et al., *Experimental Eye Research*, 65, 575-589 (1997)). FasL expression in the retina inhibits growth of blood vessels beneath the retina (Kaplan et al., supra), by inducing apoptosis in vascular endothelial cells that are known to express the Fas antigen. The loss of FasL expression in this region may be a predisposing factor in age related macular degeneration, allowing vessels to localize beneath the retina after penetration of Bruch's membrane. This process may lead to retinal detachment and visual loss.

FasL is also expressed in the cornea. Corneas that did not express functional FasL (gld) showed significantly greater neovascularization than normal corneas. In addition, engagement of Fas on vessels growing in vitro prevents vascular extension. These results suggest that FasL regulates neovascularization by engaging Fas on growing vessels and inducing apoptosis of the Fas+ vascular endothelial cells. Fas/FasL interaction is also required for the antiangiogenic effects of IL-12 and IL-2 when treating murine renal carcinoma (Wigginton, J. M., et al., *J Clin Invest.*, 108, 51-62 (2001)).

Corneal neovascularization may be due to a complex interplay between several anti-angiogenic factors and Fas. This is evident from the fact that while gld and lpr mice are less prone to spontaneous neovascularization, normal development of eye is unaffected. This is similar to observations made with the immune privilege of the eye, where FasL works in concert with other inhibitory agents to control the spread of inflammation (Stuart, P. M., et al., *Invest Ophthalmol Vis Sci.*, 44, 93-98 (2003)). The role of FasL seems to be critical when the eye is challenged or stimulated with an agent that induced inflammation (Griffith et al., 1995, supra; Kaplan et al., supra) or growth factors such FGF, HGF etc. (Stuart, et. al., supra).

Recently, an inhibitor responsible for the avascularity of ocular compartments was identified in the cornea as pigment epithelium-derived factor (PEDF) (Dawson, D. W., et al., *Science*, 285, 245-48 (1999)). This protein has been shown to have neurotrophic activity (Tombran-Tink, J., et al., *J Neurosci*, 15, 4992-5003 (1995); Taniwaki, T., et al., *J Neurochem*, 68, 26-32 (1997)) but is now known as a potent anti-angiogenic molecule (Gettins, P. G., et al., *Biol Chem*, 383, 1677-82 (2002); Simonovic, M., et al., *Proc Natl Acad Sci USA*, 98, 11131-35 (2001)). It seems to be a constitutive component of ocular compartments, and neutralization of its activity permits new vessel growth into the central cornea (Dawson et al., supra). Apoptosis in endothelial cells is associated with the activity of PEDF (Stellmach, V., et al., *Proc Natl Acad Sci USA*, 98, 2593-2597 (2001); Volpert, O. V., et al., *Nat Med*, 8, 349-357 (2002)). It has been shown that PEDF inhibitory function is orchestrated via upregulation of Fas (Volpert, O. V., et al., supra) in the cornea to inhibit spontaneous neovascularization and limit induction of angiogenesis.

The pattern of Fas L expression in the eye and the results obtained when FasL expression is modified in ocular tissue suggest that fodifying Fas function might be useful for various eye related pathologies. Altering Fas function in the eye may be a useful strategy, for example, for inhibiting corneal neovascularization.

The present inventors have undertaken a structural analysis Fas-FasL interactions. The inventors have developed an interaction model of FasL and Fas created by computer assisted modeling and designed peptide mimetics based on the deduced secondary structural features of Fas. The understanding of Fas-FasL recognition features at the atomic level has allowed the inventors to design mimetics that modulate Fas signaling functions and can thus be used to treat Fas pathologies.

Accordingly, the present inventors have identified and developed peptidomimetics that alter Fas function and will therefore have therapeutic applications against disease states mediated by Fas. The mimetics were effective in inhibiting β-FGF induced corneal neovascularization in vivo, demonstrating that Fas-FasL interaction plays a significant role in regulating extension of new blood vessels into the cornea, and indicating that Fas is a therapeutic target for eye related pathologies. The in vivo biological activity of the mimetics was also validated in a murine model of Fas-dependent Con A induced hepatitis injury. Accordingly, the mimetics are therefore also useful as therapy for fulminant hepatitis.

\* \* \*

The citation and/or discussion of a reference in this section, and throughout this specification, shall not be construed as an admission that such reference is prior art to the present invention.

SUMMARY OF THE INVENTION

In certain embodiments, the invention provides an exocyclic peptide having an amino acid sequence of a Fas surface domain that interacts with FasL.

In certain embodiments, the invention provides a Fas mimetic represented by the formula (I)

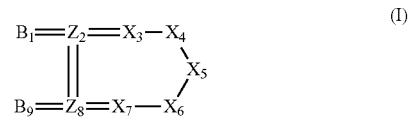

wherein:
- $B_1$ and $B_9$ are independently a peptide of 1-6 amino acids, at least one of which is a hydrophobic amino acid, an aromatic moiety or a heteroaromatic moiety,
- $Z_2$ is a moiety that is capable of forming a covalent linkage with $B_1$, $X_3$ and $Z_8$,
- $Z_8$ is a moiety that is capable of forming a covalent linkage with $B_9$, $X_7$ and $Z_2$,
- $X_3$ is a hydrophilic amino acid or a bond,
- $X_4$ is an amino acid selected from aspartic acid or glutamic acid,
- $X_5$ is an amino acid selected from aspartic acid or glutamic acid,
- $X_6$ is an amino acid selected from the group consisting of histidine, lysine, arginine, asparagine or glutamine,
- $X_7$ is an aromatic moiety or a heteroaromatic moiety,
- "—" is a covalent linkage comprising an amide, substituted amide or an isostere of amide thereof, and
- "=" is a covalent linkage,
- or a pharmaceutically acceptable salt, metabolite or prodrug thereof.

Preferably, the mimetic of formula (I) is a peptide comprising an amino sequence selected from the group consisting of YCDEGHLCY (SEQ ID NO: 1), YCDEGLCY (SEQ ID NO: 2), YCDEGYFCY (SEQ ID NO: 3), YCDEGEYCY (SEQ ID NO: 4), YCDEHFCY (SEQ ID NO:5), YCDEHGLCY (SEQ ID NO: 6), YCDEHGQCY (SEQ ID NO: 7), YCDEKFCY (SEQ ID NO: 8), and YCDEQFCY (SEQ ID NO: 9), wherein the cysteine residues of said peptide are preferably joined by a covalent bond to form a cyclic peptide. More preferably, the mimetic of formula (I) is a peptide comprising an amino sequence selected from the group consisting of YCDEHFCY (SEQ ID NO: 5), YCDEKFCY (SEQ ID NO: 8) and YCDEQFCY (SEQ ID NO: 9) wherein the cysteine residues of said peptide are preferably joined by a covalent bond to form a cyclic peptide.

In other embodiments, the invention provides mimetics comprising an amino acid sequence selected from the group consisting of YCNSTVCY (SEQ ID NO: 10), YCDKAEHFCY (SEQ ID NO: 11), YCNTRTQNTCY (SEQ ID NO: 12), YCQEKEYCY (SEQ ID NO: 13), and YCQERKEYCY (SEQ ID NO: 14).

In other embodiments, the invention is directed to a method of preventing or treating a FAS-related pathology comprising administering to a mammal (e.g., a human) suffering from said FAS-related pathology a therapeutically effective amount of the foregoing mimetics.

The invention also provides pharmaceutical compositions comprising the aforementioned mimetics.

In other embodiments, the invention is directed to a method of inhibiting Fas receptor-Fas ligand interaction comprising exposing Fas or FasL to an effective amount of the aforementioned mimetics to inhibit said interaction.

BRIEF DESCRIPTION OF THE DRAWINGS

FIG. 1A-B depicts the three dimensional structure of the binding site in FasL/Fas complex. (A) Interaction between a FasL dimer and Fas peptide mimetics Kp1, Kp2, Kp3, Kp4 and Kp7. (B) Putative solution structure of peptide mimetic Kp7-6.

DETAILED DESCRIPTION

Figure 2A:
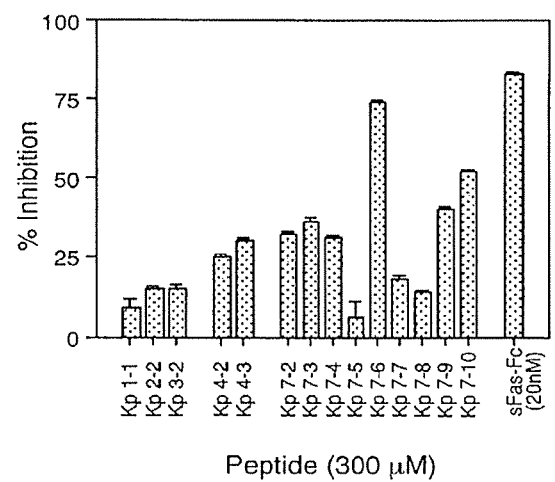
FIG. 2A-B illustrates inhibition of FasL binding to Fas-receptor by exocyclic mimetics in a binding assay.
Figure 2B:
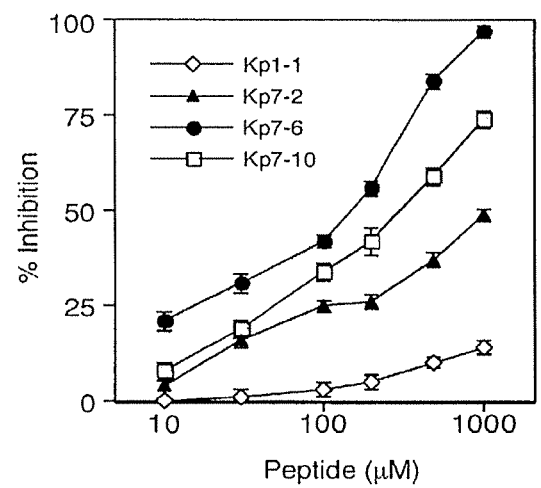
Figure 3A:
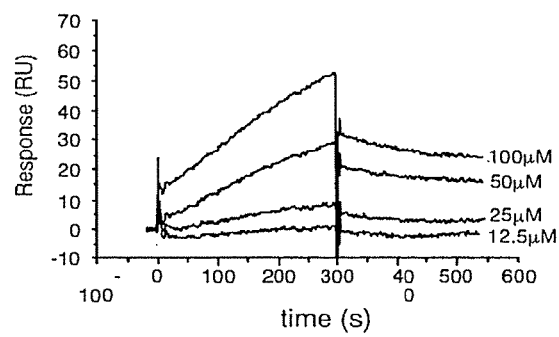
FIG. 3A-B depicts a surface plasmon resonance (biosensor) analysis of mimetic binding to immobilized FasL.
Figure 3B:
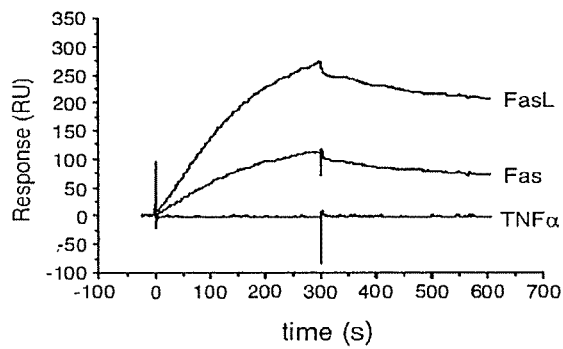

The present invention is concerned with mimetics that are antagonists of the Fas receptor (Fas)-Fas ligand (FasL) signaling system and methods of using such mimetics. The invention is based in part on the findings that sites on Fas that function in the binding of FasL can be identified by comparison to the TNF receptor and that peptide mimetics of the sites identified on Fas act to inhibit binding of FasL to Fas and inhibit Fas function, i.e., the mimetics are antagonists of FasL binding and of Fas signaling and function. The mimetics are therefore useful in the treatment of Fas-related pathologies.

Hence, the invention provides exocyclic peptide mimetics comprising an amino acid sequence of a Fas surface domain that interacts with FasL or derived from an amino acid sequence of a Fas surface domain that interacts with FasL.

The invention provides Fas mimetics represented by formula (I)

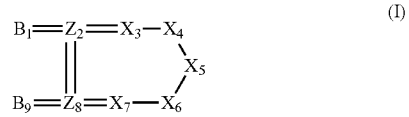

wherein:
$B_1$ and $B_9$ are independently a peptide of 1-6 amino acids, at least one of which is a hydrophobic amino acid, an aromatic moiety or a heteroaromatic moiety, $Z_2$ is a moiety that is capable of forming a covalent linkage with $B_1$, $X_3$ and $Z_8$,
$Z_8$ is a moiety that is capable of forming a covalent linkage with $B_9$, $X_7$ and $Z_2$,
$X_3$ is a hydrophilic amino acid or a bond,
$X_4$ is an amino acid selected from aspartic acid or glutamic acid,
$X_5$ is an amino acid selected from aspartic acid or glutamic acid,
$X_6$ is an amino acid selected from the group consisting of histidine, lysine, arginine, asparagine or glutamine,
$X_7$ is an aromatic moiety or a heteroaromatic moiety,
"—" is a linkage comprising an amide, substituted amide or an isostere of amide thereof, and
"=" is a covalent linkage,
or a pharmaceutically acceptable salt, metabolite or prodrug thereof.

$B_1$ and $B_9$ independently are exocyclic portions of mimetics of formula (I) that are comprised of, e.g., exocyclic amino acid residues. $Z_2$, $X_3$, $X_4$, $X_5$, $X_6$, $X_7$ and $Z_8$ comprise the cyclicized portion of mimetics of formula (I). $Z_2$ and $Z_8$ are further linking moieties, preferably linking amino acids.

Preferably, Fas mimetics of the invention are conformationally restrained peptides. Most preferably, such conformationally restrained peptides are cyclicized peptides comprising a cyclicized portion, one or more exocyclic region, one or more linking moiety and an active region.

Independent preferred moieties for the formula I are as follows: $Z_2$ is cysteine; $Z_8$ is cysteine; $X_3$ is a bond; $X_4$ is aspartic acid; $X_5$ is glutamic acid; $X_7$ is phenylalanine; and $X_7$ is an aromatic amino acid.

The following are also independent preferences: $B_1$ is tyrosine; $B_9$ is tyrosine; both $B_1$ and $B_9$ are tyrosine; $B_1$ is —$R_1$—$R_2$, where $R_1$ is an aromatic amino acid linked to $Z_2$ and $R_2$ is a peptide of 1-5 amino acids; $B_9$ is —$R_3$—$R_4$, where $R_3$ is an aromatic acid linked to $Z_8$ and $R_4$ is a peptide of 1-5 amino acids.

Also preferred is a mimetic of formula (I) comprising an amino sequence selected from the group consisting of YCDE-GHLCY (SEQ ID NO: 1), YCDEGLCY (SEQ ID NO: 2), YCDEGYFCY (SEQ ID NO: 3), YCDEGEYCY (SEQ ID NO: 4), YCDEHFCY (SEQ ID NO: 5), YCDEHGLCY (SEQ ID NO: 6), YCDEHGQCY (SEQ ID NO: 7), YCDEKFCY (SEQ ID NO: 8) and YCDEQFCY (SEQ ID NO: 9), wherein the cysteine residues of said amino acid sequence are joined by a covalent bond, to form a cyclic peptide. More preferably, a mimetic of formula (I) comprises an amino sequence selected from the group consisting of YCDEHFCY (SEQ ID NO: 5), YCDEKFCY (SEQ ID NO: 8) and YCDEQFCY (SEQ ID NO: 9), wherein the cysteine residues of said amino acid sequence are joined by a covalent bond, to form a cyclic peptide.

Also provided for use in the invention is a mimetic comprising an amino acid sequence selected from the group consisting of YCNSTVCY (SEQ ID NO: 10), YCDKAEHFCY (SEQ ID NO: 11), YCNTRTQNTCY (SEQ ID NO: 12), YCQEKEYCY (SEQ ID NO: 13), and YCQERKEYCY (SEQ ID NO: 14).

Preferred mimetics provided in the invention are in the range of about 5 to about 100 amino acids in length. Further preferred mimetics provided in the invention are in the range of about 5 to about 50 amino acids in length, or in the range of about 10 to about 50 amino acids in length. Still further preferred mimetics provided in the invention are in the range of about 5 to about 40 amino acids in length, or in the range of about 10 to about amino acids in length. Still further preferred mimetics provided in the invention are in the range of about 5 to about 30 amino acids in length, or in the range of about 10 to about 30 amino acids in length. Still further preferred mimetics provided in the invention are in the range of about 5 to about 20 amino acids in length, or in the range of about 10 to about amino acids in length. Most preferred mimetics provided in the invention are in the range of about 5 to about 10 amino acids in length.

Definitions:

Amino acid residues used in the present invention may be recited by their full name or by reference to either the three letter or single letter amino acid code (see, e.g., Table 5.1 of Mathews & van Holde, *Biochemistry*, Second Edition (Benjamin/Cumings Publishing Company, Inc., New York) at page 131). The mimetics that are encompassed within the scope of the invention are partially defined in terms of amino acid residues of designated classes. The amino acids may be generally categorized into three main classes: hydrophilic amino acids, hydrophobic amino acids and cysteine-like amino acids, depending primarily on the characteristics of the amino acid side chain. These main classes may be further divided into subclasses. Hydrophilic amino acids include amino acids having acidic, basic or polar side chains. Hydrophobic amino acids include amino acids having aromatic or apolar side chains. Apolar amino acids may be further subdivided to include, among others, aliphatic amino acids. The definitions of the classes of amino acids as used herein are as follows:

The term "hydrophobic amino acid" refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

The term "aromatic amino acid" refers to a hydrophobic amino acid having a side chain containing at least one ring having a conjugated pi-electron system (aromatic group). The aromatic group may be further substituted with substituent groups such as alkyl, alkenyl, alkynyl, hydroxyl, sulfanyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

The term "hydrophilic amino acid" refers to an amino acid having a side chain that is capable of bonding to solvent molecules in an aqueous solution. Examples of genetically encoded hydrophilic amino acids include Ser and Lys. Examples of non-encoded hydrophilic amino acids include Cit and hCys.

The term "heteroaromatic moiety" refers to an aromatic moiety wherein one or more of the ring carbon atoms is replaced with another atom such as, for example, nitrogen, oxygen or sulfur. Typical heteroaromatic moieties include, but are not limited to, pyran, pyrazole, pyridine, pyrrole, pyrazine, pyridazine, pyrimidine, pyrrolizine, quinazoline, quinoline, quinolizine, quinoxaline, selenophene, thiophere, tellurophene, xanthene, and the like.

Additional examples of amino acids and related compounds are found in U.S. Pat. No. 6,265,535.

As used herein, the term "mimetic" refers to compounds which mimic the activity of a peptide. Mimetics may themselves be peptides. Mimetics may also be non-peptides and/or may comprise amino acids linked by non-peptide bonds, e.g., without limitation, psi bonds (see, e.g., Benkirane, N., et al. *J. Biol. Chem.*, 271:33218-33224 (1996)). U.S. Pat. No. 5,637, 677 and its parent applications contain detailed guidance on the production of mimetics. Preferred mimetics are "conformationally constrained" peptides. Also preferred are cyclic mimetics. Further preferred are cyclic mimetics comprising at least one exocyclic domain, a linking moiety (e.g., a linking amino acid) and an active region.

As used herein, the terms "constrained peptides" and "conformationally constrained peptides" are used interchangeably and are meant to refer to peptides which, e.g., through intramolecular bonds, are conformationally stable and remain in a restricted conformation.

As used herein, the term "exocyclic amino acid residue" is meant to refer to an amino acid residue that is linked directly or indirectly to a cyclicized peptide but which is not within the portion of the peptide that makes up the circularized structure.

As used herein, the term "exocyclic portion" is meant to refer to an amino acid sequence having one or more amino acid residues which are linked to cyclicized peptide but which are not within the portion of the peptide that makes up the circularized structure.

As used herein, the term "linking moiety" is meant to refer to a molecular component or functional group which is capable of forming bonds with three amino acids.

As used herein, the term "linking amino acid residue" is meant to refer to an amino acid residue that is a linking moiety.

As used herein, the term "active region" is meant to refer to the amino acid sequence of the portion of a mimetic that directly interacts with a receptor or receptor ligand, wherein the interaction is characterized by an affinity between the active region of the mimetic and the receptor or receptor ligand.

The term "Fas mimetic" refers to a peptide mimetic that is derived from a Fas peptide; i.e., a Fas mimetic of the invention is a compound that mimics a Fas peptide (a peptide derived from Fas). Preferred Fas mimetics are mimetics of a peptide derived from and/or corresponding to a Fas surface domain. Further preferred are Fas mimetics that are mimetics of a peptide derived from and/or corresponding to a Fas surface loop domain. Exemplary Fas peptides are provided, infra, in Table 1. Particularly preferred Fas mimetics of the invention are mimetics of Fas Kp7 surface domain peptides.

Fas mimetics are preferably derived from human or mouse Fas. More preferably, Fas mimetics are derived from human Fas, e.g., without limitation, human Fas. Most preferably, mimetics are derived from human Fas with the mature amino acid sequence:

```
                                          (SEQ ID NO: 15)
RLSSKSVNAQVTDINSKGLELRKTVTTVETQNLEGLHH

DGQFCHKPCPPGERKARDCTVNGDEPDCVPCQEGKEY

TDKAHFSSKCRRCRLCDEGHGLEVEINCTRTQNTKCRC

KPNFFCNSTVCEHCDPCTKCEHGIIKECTLTSNTKCKEE

GSRSNLGWLCLLLLPIPLIVWVKRKEVQKTCRKHRKEN

QGSHESPTLNPETVAINLSDVDLSKYITTIAGVMTLSQV

KGFVRKNGVNEAKIDEIKNDNVQDTAEQKVQLLRNW

HQLHGKKEAYDTLIKDLKKANLCTLAEKIQTIILKDITS

DSENSNFRNEIQSLV
```

Preferred Fas mimetics of the invention are capable of interacting with (e.g., binding to) either Fas, FasL or both Fas and FasL. Fas mimetics may therefore modulate Fas activity (in particular, Fas mediated signaling), for example as antagonists, agonists, or inverse agonists. For example, in certain embodiments a Fas mimetic of the invention may inhibit binding of FasL to Fas, and may thereby inhibit Fas activity. In other embodiments (that are preferably practiced either in the absence of or at very low concentrations of FasL) a Fas mimetic of the invention may bind to and activate Fas.

As used herein, the term "surface domain" refers to a domain of a protein comprising one or more solvent accessible amino acid. A surface domain make include, e.g., 1, 2, 3, 4, 5, 6, 7, 8, 9, 10, 11, 12, 13, 14, 15, 16, 17, 18, 19, or 20 solvent accessible amino acids. A surface domain may also include greater than 20 solvent accessible amino acids. Preferably, each amino acid in a surface domain is a solvent accessible amino acid. Solvent accessible amino acids and hence surface domains may be identified using methods well known in the art (see, e.g., Jones et al., *J. Mol. Biol.*, 272:121-132 (1997) and Samanta, U. et al., *Prot. Eng.*, 15:659-667 (2002)).

Solvent accessibility of an amino acid is expressed as a value from 0.0 (buried) to 1.0 completely accessible. Preferably, a surface domain comprises at least one amino acid with a solvent accessibility of at least about 0.3. More preferably, a surface domain comprises at least one amino acid with a solvent accessibility of at least about 0.4, 0.5, 0.6 or 0.7. More preferably, a surface domain comprises at least one amino acid with a solvent accessibility of at least about 0.8, 0.9 or 0.95. Further preferred is where a surface domain comprises about 2, 3, 4, 5, 6, 7, 8, 9, or 10 amino acids with a solvent accessibility of at least 0.3, or comprises at least about 2, 3, 4, 5, 6, 7, 8, 9, or 10 amino acids with a solvent accessibility of at least about 0.3. Further preferred is where a surface domain comprises about 2, 3, 4, 5, 6, 7, 8, 9, or 10 amino acids with a solvent accessibility of at least about 0.4, 0.5, 0.6, or 0.7, or comprises at least about 2, 3, 4, 5, 6, 7, 8, 9, or 10 amino acids with a solvent accessibility of at least about 0.4, 0.5, 0.6, or 0.7. Further preferred is where a surface domain comprises about 2, 3, 4, 5, 6, 7, 8, 9, or 10 amino acids with a solvent accessibility of at least about 0.8, 0.9, or 0.95, or comprises at least about 2, 3, 4, 5, 6, 7, 8, 9, or 10 amino acids with a solvent accessibility of at least about 0.8, 0.9, or 0.95.

Also preferred is where a surface domain consists of about 2, 3, 4, 5, 6, 7, 8, 9, or 10 amino acids with a solvent accessibility of at least about 0.3, or consists of at least about 2, 3, 4, 5, 6, 7, 8, 9, or 10 amino acids with a solvent accessibility of at least about 0.3. Further preferred is where a surface domain consists of about 2, 3, 4, 5, 6, 7, 8, 9, or 10 amino acids with a solvent accessibility of at least about 0.4, 0.5, 0.6, or 0.7, or consists of at least about 2, 3, 4, 5, 6, 7, 8, 9, or 10 amino acids with a solvent accessibility of at least about 0.4, 0.5, 0.6, or 0.7. Further preferred is where a surface domain consists of about 2, 3, 4, 5, 6, 7, 8, 9, or 10 amino acids with a solvent accessibility of at least about 0.8, 0.9, or 0.95, or consists of at least about 2, 3, 4, 5, 6, 7, 8, 9, or 10 amino acids with a solvent accessibility of at least about 0.8, 0.9, or 0.95.

As used herein, the term "treatment" refers to administering an active agent to lessen the severity or the likelihood of the re-occurrence of a pre-existing condition. Hence, "treatment" encompasses, for example and without limitation, ameliorating at least one symptom associated with a condition or reducing the rate of occurrence or re-occurrence of a condition.

As used herein, the term "preventing" refers to the lessening of the likelihood of the occurrence of a condition.

As used herein, a "subject in need of treatment of" or a "subject suffering from" a condition is a mammal (e.g., human) that manifests at least one symptom of a condition or that is at risk of developing or re-developing the particular condition to be treated.

As used herein, a "therapeutically effective amount" of an agent is an amount sufficient to ameliorate at least one symptom associated with a pathological, abnormal or otherwise undesirable condition, an amount sufficient to prevent or lessen the probability that such a condition will occur or re-occur, or an amount sufficient to delay worsening of such a condition.

As used herein, a "Fas-related pathology" is a pathological condition that can be treated by increasing or decreasing activity (i.e., signaling) of Fas. A "Fas-related pathology" is preferably treated with an antagonist of Fas activity. More preferably, said antagonist binds to one or both of Fas or FasL to lower Fas activity. Alternatively, in certain embodiments, a "Fas-related pathology" may be treated with an agonist of Fas activity. Examples of "Fas-related pathologies" include, without limitation, pathologies related to lymphocyte apoptosis leading to abnormal lymphoproliferation and autoimmunity. Additional examples include, without limitation, aging and cell death (e.g., in the skin and other organs), visual loss, rheumatoid arthritis, Sjogren's syndrome, multiple, viral hepatitis, renal injury, HIV infection, and angiogenesis. See also Famularo et al. supra. The inhibition of FasL and Fas antigen interactions has also been used to prevent transplantation rejections. Mimetics of the invention which inhibit the binding of Fas with FasL may be used to augment immune responses in certain settings.

In a preferred embodiment, memetics of the invention are used to treat visual loss or other ocular disorder either with or without coincident neovascularization. In a preferred embodiments, the mimetics of the invention are used to treat visual loss or other ocular disorder with coincident neovascularization. Examples of ocular disorder include, without limitation, macular degeneration, e.g, age-related macular degeneration.

A "metabolite" of a compound disclosed herein is a derivative of a compound which is formed when the compound is metabolized. The term "active metabolite" refers to a biologically active derivative of a compound which is formed when the compound is metabolized. The term "metabolized" refers to the sum of the processes by which a particular substance is changed in the living body. In brief, all compounds present in the body are manipulated by enzymes within the body in order to derive energy and/or to remove them from the body. Specific enzymes produce specific structural alterations to the compound. For example, cytochrome P450 catalyses a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulfhydryl groups. Further information on metabolism may be obtained from *The Pharmacological Basis of Therapeutics*, 9th Edition, McGraw-Hill (1996), pages 11-17.

Metabolites of the compounds disclosed herein can be identified either by administration of compounds to a host and analysis of tissue samples from the host, or by incubation of compounds with hepatic cells in vitro and analysis of the resulting compounds. Both methods are well known in the art.

A "prodrug" of a compound disclosed herein is an inactive substance that converts into an active form of the disclosed compounds in vivo when administered to a mammal.

The compounds of the present invention are related to mimetics of Fas as disclosed above, including all enantiomers, diastereomers, crystalline forms, hydrates, solvates or pharmaceutically acceptable salts thereof, as well as active metabolites of these mimetics having the same type of activity.

An antagonist of Fas is a substance which diminishes or abolishes the effect of a ligand (agonist) which typically activates Fas receptor, e.g., FasL. The antagonist may be, for example, a chemical antagonist, a pharmacokinetic antagonist, an antagonist by receptor block, a non-competitive antagonist or a physiological antagonist. In a preferred embodiment, the antagonist is a chemical antagonist or an antagonist by receptor block. The antagonist is preferably a Fas mimetic. Further preferred, the antagonist is a mimetic of Fas peptide Kp1, Kp2, Kp3, Kp4, or Kp7.

A chemical antagonist is a substance wherein the antagonist binds the ligand in solution so the effect of the ligand is lost. A pharmacokinetic antagonist is one which effectively reduces the concentration of the ligand at its site of action, for example, by increasing the rate of metabolic degradation of the active ligand. Antagonism by receptor-block involves two important mechanisms: reversible competitive antagonism and irreversible, or non-equilibrium competitive antagonism. Reversible competitive antagonism occurs when the rate of dissociation of the antagonist molecules is sufficiently high such that, on addition of the ligand, displacement of chemical antagonist molecules from the receptors effectively occurs. Of course the ligand cannot evict a bound antagonist molecule, or vice versa. Irreversible or non-equilibrium competitive antagonism occurs when the antagonist dissociates very slowly, or not at all, from the receptor with the result that no change in the antagonist occupancy takes place when the ligand is applied. Thus, the antagonism is insurmountable. Non-competitive antagonism describes the situation where the antagonist exerts its blocking action at some point in the signal transduction pathway leading to the production of a response by the ligand.

Mimetics of the invention are preferably antagonists of Fas. More preferably, mimetics used in the invention are selective antagonists of Fas. A selective antagonist of Fas is one which antagonizes Fas, but antagonizes other receptors of the TNF family of receptors only weakly or substantially not at all. Most preferred mimetic antagonists are those which selectively antagonize Fas receptor at low concentration, for example, those that cause a level of antagonism of 50% or greater at a concentration of 1000 mM or less. Selective Fas mimetic antagonists can thus typically exhibit at least a 10-fold, preferably a 100-fold and most preferably a 1000-fold greater activity for Fas than at other TNF receptors.

Preferred Embodiments:

Fas mimetics of the invention preferably have one or more of the following properties:

(1) Significant Inhibition of FasL Binding to Fas:

Mimetics preferably exhibit antagonist potency (measured as $IC_{50}$) between 1 nM and 500 mM. Without limiting the present disclosure, as described in more detail below, potency may be measured by determining the antagonist activity of mimetics in vivo or in vitro, including cell extracts or fractions of extracts. Inhibitory potency may also be determined using, as non-limiting examples, native or recombinant Fas, and/or soluble Fas. Fas binding may be determined using methods that are well known to those skilled in the art, such as ELISA and proliferation by MTT (Hansen et al., *J. Immunol. Methods* 199, 203-210 (1989))

(2) Selectivity:

Preferred mimetics exhibit at least about 10-fold greater antagonist potency for Fas, compared to other TNF receptors. More preferred are compounds that exhibit about 100-fold greater antagonist for Fas, compared to other TNF receptors. Most preferred are compounds that exhibit about 1000-fold greater antagonist for Fas, compared to other TNF receptors.

(3) Binding to FasL:

Mimetics preferably bind to FasL and inhibit the interaction of FasL and Fas. The binding affinity of mimetics to FasL can be described by different parameters, e.g., $k_{on}$, $k_{off}$ and $K_D$. In preferred embodiments, the mimetics have affinities for FasL represented by values of $k_{on}$ greater than $10 \text{ M}^{-1}\text{s}^{-1}$, $k_{off}$ of less than $10^{-3} \text{ s}^{-1}$ or $K_D$ of less than $10^{-4}$ M. More preferably, mimetics have affinities for FasL represented by values of $k_{on}$ greater than $10^2 \text{ M}^{-1}\text{s}^{-1}$, $k_{off}$ of less than $10^{-4} \text{ s}^{-1}$ or $K_D$ of less than $10^{-5}$ M. Most preferably, mimetics have affinities for FasL represented by values of $k_{on}$ greater than $10^3 \text{ M}^{-1}\text{s}^{-1}$, $k_{off}$ of less than $10^{-5} \text{ s}^{-1}$ or $K_D$ of less than $10^{-6}$ M.

Accordingly, mimetics having one or more of these properties are candidates for use in treatment of Fas-related pathologies in mammals and especially in humans.

Mimetics with one or more of the above properties can further be tested for biological activity using assays that measure Fas function in vitro or in vivo.

Measurement of mimetic biological activity can be determined in vitro, e.g., by measuring inhibition of Fas-L induced cytotoxicity or by inhibition of Fas-L induced apoptosis in cell culture, as described below in Examples 4 and 5, respectively. Alternatively, mimetic biological activity may also be measured by directly or indirectly measuring signaling aspects of Fas activity, such as caspase activity, NF-κB activation, and/or other downstream mediators of Fas signaling.

A useful animal model for measurement of Fas activity in vivo is the Con A-induced hepatitis model described in Example 6. This assay is a murine model of human autoimmune hepatitis. (Tiegs, G. et al. *J Clin Invest* 90, 196-203 (1992)). T cell activation plays a crucial role in the process of Con A-induced hepatitis, because severe combined immunodeficiency disorder (SCID) mice and athymic nude mice, which lack mature T cells, are resistant to the damage induced by Con A. (Tiegs et al. supra; Mizuhara, H. et al. *J Exp Med* 179, 1529-1537 (1994). The hepatic injury seems to be induced by several different mechanisms, such as those involving Fas-FasL (Seino, K. et al. *Gastroenterology* 113, 1315-1322 (1997); Tagawa, Y. et al. *Eur J Immunol* 28, 4105-4113 (1998); Tagawa, Y. et al. *J Immunol* 159, 1418-1428 (1997)), the perforin-granzyme system (Watanabe, Y. et al. *Hepatology* 24, 702-710 (1996)), IFN-γ (Tagawa et al. supra; Kusters, S. et al. *Gastroenterology* 111, 462-471 (1996)) and TNF-α-mediated cytotoxicity (Mizuhara et al. supra; Toyabe, S. et al. *J Immunol* 159, 1537-1542 (1997); Gantner, F. et al. *Exp Cell Res* 229, 137-146 (1996); Gantner, F. et al. *Hepatology* 21, 190-198 (1995); Kusters, S. et al. *Eur J Immunol* 27, 2870-2905 (1997); Ksontini, R. et al. *J Immunol* 160, 4082-4089 (1998)). (Mizuhara, H. et al. *J Exp Med* 179, 1529-1537 (1994). Hepatic damage is primarily dependent upon the Fas-FasL system, because FasL defective gld/gld mice or Fas defective lpr/lpr mice are resistant to liver injury induced by Con A treatment. (Tagawa et al. supra; Tagawa et al. supra).

Design of Mimetics:

According to preferred embodiments a mimetic is designed based on a known region of FAS. In preferred embodiments, the mimetic mimics an extracellular domain of an Fas, more preferably a cystine knot region of Fas. Most preferably, the mimetic is based on the Fas Kp7 domain.

Identification of Fas peptides on which to base mimetics can be performed using computer modeling and structural analysis. For instance, Example 1, infra, describes one embodiment in which an interaction model of FasL and Fas was created by computer assisted modeling, and used to design peptide mimetics based on deduced secondary structural features of Fas. In such an embodiment, a skilled user may define optimal interactions of Fas surfaces that are consistent with either available biological data or structural surface complementarity. Peptide mimetics can then be designed and synthesized for all secondary structures involved in such interactions, typically corresponding to about five mimetic compounds. Each compound may be modified as described, e.g., in U.S. Pat. Nos. 6,100,377 and 6,265,535. The mimetic compounds thus obtained can then be tested, e.g., using methods described in this application, for their activity as Fas agonists or antagonists.

Reducing a macromolecule to a small molecule with similar function is a general chemical problem. There have been some attempts to design mini-proteins by transplanting functional units onto suitable scaffolds (Vita et al., *Biopolymers* 47, 93-100 (1998)) and minimizing antibodies to single chain antibodies (Magliani et al., *Nature Biotechnol.* 15, 155-158 (1997)).

It is now established that conformation constrained peptides are more bioactive than unconstrained ones. In recent years, the chemistry of peptide cyclization by solid phase synthesis and other methods has improved dramatically (Burgess et al. (1996) in *Solid phase syntheses of peptidomimetics* (American Chemical Society, Washington D.C.) pp. ORGN-157; Goodman & Shao, *Pure Appl. Chem.* 68, 1303-1308 (1996); Hanessian et al., *Tetrahedron* 53, 12789-12854 (1997); Koskinen & Hassila, *Acta Chem. Scand.* 50, 323-327 (1996); Kuhn et al., *Tetrahedron* 53, 12497-12504 (1997); Waid et al., *Tetrahedron Lett.* 37, 4091-4094 (1996); Zuckermann, *Curr. Opin. Struct. Biol.* 3, 580-584 (1993)) providing more opportunity to develop peptides into peptidomimetics.

General principles to create cyclic peptide mimetics that have been adopted and in some cases (such as eptifitimide (Integrilin) a glycoprotein llb llla inhibitor (COR Therapeutics)) have become clinically available. Aromatic residues placed at the termini of cyclically constrained small peptides increase the activity of mimetics (Takasaki et al., *Nat. Biotechnol.* 15, 1266-1270 (1997); Zhang et al., *Nature Biotechnol.* 14, 472-475 (1996)). Employing such modifications has allowed creation of high affinity mimetics of antibody mimics based on CDRs (Park et al., *Nature Biotechnol.* 18, 194-198 (2000)), CD4 (Zhang et al., *Nature Biotechnol.* 15, 150-154 (1997)), IL4 receptor loop mimetics, anti-CD3 antibody mimics, and TNF cystine knot mimetic that affect TNFα binding to its receptor (Takasaki et al., *Nature Biotechnol.* 15, 1266-1270 (1997)).

Chemical Synthesis:

The mimetics of the invention may be prepared using virtually any art-known technique for the preparation of peptides and peptide analogues. For example, the peptides may be prepared in linear or non-cyclized form using conventional solution or solid phase peptide syntheses and cyclized using standard chemistries. Preferably, the chemistry used to cyclize the peptide will be sufficiently mild so as to avoid substantially degrading the peptide. Suitable procedures for synthesizing the peptides described herein as well as suitable chemistries for cyclizing the peptides are well known in the art.

Formation of disulfide linkages, if desired, is generally conducted in the presence of mild oxidizing agents. Chemical, enzymatic or photolytic oxidation agents may be used. Various methods are known in the art, including those described, for example, by Tam, J. P. et al., 1979, *Synthesis* 955-957; Stewart et al., 1984, *Solid Phase Peptide Synthesis*, 2d Ed., Pierce Chemical Company Rockford, Ill.; Ahmed et al., 1975, *J. Biol. Chem.* 250:8477-8482; and Pennington et al., 1991 *Peptides* 1990 164-166, Giralt and Andreu, Eds., ESCOM Leiden, The Netherlands. An additional alternative is described by Kamber et al., 1980, *Helv Chim Acta* 63:899-915. A method conducted on solid supports is described by Albericio, 1985, *Int. J. Peptide Protein Res.* 26:92-97. Any of these methods may be used to form disulfide linkages in the peptides of the invention.

Recombinant Synthesis:

If the peptide is composed entirely of gene-encoded amino acids, or a portion of it is so composed, the peptide or the relevant portion may also be synthesized using conventional recombinant genetic engineering techniques. The isolated peptides, or segments thereof, are then condensed, and oxidized, as previously described, to yield a cyclic peptide.

For recombinant production, a polynucleotide sequence encoding a linear form of the peptide is inserted into an appropriate expression vehicle, i.e., a vector which contains the necessary elements for the transcription and translation of the inserted coding sequence, or in the case of an RNA viral vector, the necessary elements for replication and translation. The expression vehicle is then transfected into a suitable target cell which will express the linear form of the cyclic peptide. Depending on the expression system used, the expressed peptide is then isolated by procedures well-established in the art. Methods for recombinant protein and peptide production are well known in the art (see, e.g., Maniatis et al., 1989, *Molecular Cloning A Laboratory Manual*, Cold Spring Harbor Laboratory, N.Y.; and Ausubel et al., 1989, *Current Protocols in Molecular Biology*, Greene Publishing Associates and Wiley Interscience, N.Y.).

A variety of host-expression vector systems may be utilized to express the peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems.

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding the peptides of the invention may be driven by any of a number of promoters. For example, viral promoters such as the 35S RNA and 19S RNA promoters of CaMV (Brisson et al., 1984, *Nature* 310:511-514), or the coat protein promoter of TMV (Takamatsu et al., 1987, *EMBO J.* 6:307-311) may be used; alternatively, plant promoters such as the small subunit of RUBISCO (Coruzzi et al., 1984, *EMBO J.* 3:1671-1680; Broglie et al., 1984, *Science* 224:838-843) or heat shock promoters, e.g., soybean hsp17.5-E or hsp17.3-B (Gurley et al., 1986, *Mol. Cell. Biol.* 6:559-565) may be used. These constructs can be introduced into plant cells using Ti plasmids, Ri plasmids, plant virus vectors, direct DNA transformation, microinjection, electroporation, etc. For reviews of such techniques see, e.g., Weissbach & Weissbach, 1988, *Methods for Plant Molecular Biology*, Academic Press, NY, Section VIII, pp. 421-463; and Grierson & Corey, 1988, *Plant Molecular Biology*, 2d Ed., Blackie, London, Ch. 7-9.

In one insect expression system that may be used to produce the peptides of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (e.g., see Smith et al., 1983, *J. Virol.* 46:584; Smith, U.S. Pat. No. 4,215,051). Further examples of this expression system may be found in Current *Protocols in Molecular Biology*, Vol. 2, Ausubel et al., eds., Greene Publish. Assoc. & Wiley Interscience.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. (e.g., See Logan et al., 1984, *Proc. Natl. Acad. Sci. USA* 81:3655-3659). Alternatively, the vaccinia 7.5 K promoter may be used, (see, e.g., Mackett et al., 1982, *Proc. Natl. Acad. Sci. USA* 79:7415-7419; Mackett et al., 1984, *J. Virol.* 49:857-864; Panicali et al., 1982, *Proc. Natl. Acad. Sci. USA* 79:4927-4931).

Other expression systems for producing linear or non-cyclized forms of the cyclic peptides of the invention will be apparent to those having skill in the art.

Purification of the Peptides and Peptide Analogues:

The peptides and peptide analogues of the invention can be purified by art-known techniques such as high performance liquid chromatography, ion exchange chromatography, gel electrophoresis, affinity chromatography and the like. The actual conditions used to purify a particular peptide or analogue will depend, in part, on factors such as net charge, hydrophobicity, hydrophilicity, etc., and will be apparent to those having skill in the art.

For affinity chromatography purification, any antibody which specifically binds the peptides or peptide analogues may be used. For the production of antibodies, various host animals, including but not limited to rabbits, mice, rats, etc., may be immunized by injection with a linear or cyclic peptide. The peptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to a peptide may be prepared using any technique which provides for the production of antibody molecules by continuous cell lines in culture.

These include but are not limited to the hybridoma technique originally described by Koehler and Milstein, 1975, *Nature* 256:495-497, the human B-cell hybridoma technique, Kosbor et al., 1983, *Immunology Today* 4:72; Cote et al., 1983, *Proc. Natl. Acad. Sci. USA* 80:2026-2030 and the EBV-hybridoma technique (Cole et al., 1985, *Monoclonal Antibodies and Cancer Therapy*, Alan R. Liss, Inc., pp. 77-96 (1985)). In addition, techniques developed for the production of "chimeric antibodies" (Morrison et al., 1984, *Proc. Natl. Acad. Sci. USA* 81:6851-6855; Neuberger et al., 1984, *Nature* 312:604-608; Takeda et al., 1985, *Nature* 314:452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce cyclic peptide-specific single chain antibodies.

Antibody fragments which contain deletions of specific binding sites may be generated by known techniques. For example, such fragments include but are not limited to F(ab').sub.2 fragments, which can be produced by pepsin digestion of the antibody molecule and Fab fragments, which can be generated by reducing the disulfide bridges of the F(ab').sub.2 fragments. Alternatively, Fab expression libraries may be constructed (Huse et al., 1989, *Science* 246:1275-1281) to allow rapid and easy identification of monoclonal Fab fragments with the desired specificity for the cyclic peptide of interest.

The antibody or antibody fragment specific for the desired cyclic peptide can be attached, for example, to agarose, and the antibody-agarose complex is used in immunochromatography to purify cyclic peptides of the invention. See, Scopes, 1984, *Protein Purification Principles and Practice*, Springer-Verlag New York, Inc., NY, Livingstone, 1974, Methods Enzymology: Immunoaffinity Chromatography of Proteins 34:723-731.

Formulation and Routes of Administration:

The compounds of the invention, may be administered to a subject per se or in the form of a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active peptides or peptide analogues into preparations which can be used pharmaceutically. Proper formulation is dependent upon the route of administration chosen.

For topical administration the compounds of the invention may be formulated as solutions, gels, ointments, creams, suspensions, etc., as are well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration.

For injection, the compounds of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

Alternatively, the compounds may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the compounds can be readily formulated by combining the active peptides or peptide analogues with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compounds may take the form of tablets, lozenges, etc., formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver peptides and peptide analogues of the invention. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

As the mimetics of the invention may contain charged side chains or termini, they may be included in any of the above-described formulations as the free acids or bases or as pharmaceutically acceptable salts. Pharmaceutically acceptable salts are those salts which substantially retain the antimicrobial activity of the free bases and which are prepared by reaction with inorganic acids. Pharmaceutical salts tend to be more soluble in aqueous and other protic solvents than are the corresponding free base forms.

Effective Dosage:

The compounds of the invention will generally be used in an amount effective to achieve the intended purpose. For use to treat or prevent FAS-related pathologies, the compounds of the invention, or pharmaceutical compositions thereof, are administered or applied in a therapeutically effective amount. By therapeutically effective amount is meant an amount effective ameliorate or prevent the symptoms, or prolong the survival of, the patient being treated. Determination of a therapeutically effective amount is well within the capabilities of those skilled in the art.

For systemic administration, a therapeutically effective dose can be estimated initially from in vitro assays. For example, a dose can be formulated in animal models to achieve a circulating concentration range that includes the $IC_{50}$ as determined in cell culture (i.e., the concentration of test compound that inhibits 50% of Fas:Fas-L binding interactions). Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds which are sufficient to maintain therapeutic effect. Usual patient dosages for administration by injection range from about 0.01 to about 25 mg/kg/day, preferably from about 0.1 to about 10 mg/kg/day and more preferably from about 0.5 to about 5 mg/kg/day. Also preferred are total daily dosages from about 25 to about 1000 mg per day, preferably from about 100 to about 750 mg per day and more preferably from about 250-500 mg per day.

Therapeutically effective serum levels may be achieved by administering multiple doses each day.

In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration and the judgment of the prescribing health professional.

The therapy may be repeated intermittently while symptoms are detectable or even when they are not detectable. The therapy may be provided alone or in combination with other drugs. In the case of Fas-related pathologies, the drugs that may be used in combination with the mimetics of the invention include, but are not limited to, anti-inflammatories, steroids and antimetabolites (for example, methotrexate).

Drugs used "in combination" are administered as part of a common method of treating a given pathology. Drugs used in combination may be administered in single or separate dosage forms. Separate dosage forms may be administered at the same or different times.

Toxicity:

Preferably, a therapeutically effective dose of the compounds described herein will provide therapeutic benefit without causing substantial toxicity.

Toxicity of the compounds described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in human. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (Sec, e.g., Fingl et al., 1975, In: *The Pharmacological Basis of Therapeutics*, Ch. 1, p. 1).

EXAMPLES

The present invention is also described by means of the following examples. However, the use of these or other examples anywhere in the specification is illustrative only and in no way limits the scope and meaning of the invention or of any exemplified term. Likewise, the invention is not limited to any particular preferred embodiments described herein. Indeed, many modifications and variations of the invention may be apparent to those skilled in the art upon reading this specification and can be made without departing from its spirit and scope. The invention is therefore to be limited only by the terms of the appended claims along with the full scope of equivalents to which the claims are entitled.

Example 1

Molecular Model of a Fas Receptor Complex

Fas, a member of TNF superfamily, shares significant structural homology with the TNF receptor. The structure of the TNF receptor contains distinct "cystine-knot" repeating domains. (Naismith, J. H. et al. *Structure* 4, 1251-1262 (1996)). Loop structures in the first three domains as well as β-turns in proteins are considered to mediate roles in molecular recognition and binding. (Leszczynski, J. F. et al. *Science* 234, 849-855 (1986)). To develop a cystine-knot peptide mimetic, sites of protein-protein interaction that might be disrupted or influenced by small molecules were identified.

A molecular model of the Fas and FasL complex (FIG. 1*a*) was developed using the crystal structure of TNF receptor complex in our methodology as well as other already published models. (Watanabe-Fukunaga et al. supra; Naismith, J. H. et al. *J Biol Chem* 270, 13303-13307 (1995); Banner, D. W. et al. *Cell* 73, 431-445 (1993); Bajorath, J. *J Comput Aided Mol Des* 13, 409-418 (1999)). The overall features of the receptor-ligand interaction were noted to be very similar to that of TNF receptor ligand complex. See, U.S. Pat. No. 6,265,535. However, the ectodomain of the Fas receptor appears to be rotated about 10° compared to the transmembrane domain. Fas-FasL contact sites predicted by the molecular model are consistent with the mutation analysis data. (Beltinger, C. et al. *British Journal of Haematology* 102, 722-728 (1998)).

The Fas-FasL structural model suggested five surfaces where FasL can bind to Fas, designated Kp1, Kp2, Kp3, Kp4 and Kp7 (FIG. 1*b*), compared to such three sites identified in the TNF receptor (Takasaki et al. supra). The amino acids in the loops Kp1, 2, 3, 4 and 7 adopt well defined conformations (i.e., adopt statistically allowed conformations) as judged by Ramachandran plots (Ramachandran, G. N. et al. *Biopolymers* 6, 1255-1262 (1968); Ramachandran, G. N. et al. *Adv Protein Chem* 23, 283-438 (1968)) and profile analyses. (Zhang, K. Y. et al. *Protein Sci* 3, 687-695 (1994)).

Peptide analogs were designed from the various loop structures. Each mimetic was optimized for its ability to mimic the binding conformation of the loop and for its ring size which we have determined to be critical to reduce the inherent flexibility of mimetics. Specific features optimized included conformational mimicry between the loop structure and the mimetic, hydropathic value of the mimetics, dissociation rate (as measured from surface plasmon resonance; see., Example 3, infra), stability and solubility. A set of mimetics that were selected for biological assay is shown in Table 1.

TABLE 1

| Exocyclic Mimetics Derived from Fas | | | |
|---|---|---|---|
| Fas Receptor Peptide | | Exocyclic Mimetic | |
| Designation | Sequence* | Designation | Sequence |
| Kp1 | 119 CNSTVC 124 (SEQ ID NO: 16) | Kp1-1 | YCNSTVCY (SEQ ID NO: 10) |
| Kp2 | 77 DKAHFSSKC 85 (SEQ ID NO: 17) | Kp2-2 | YCDKAEHFCY (SEQ ID NO: 11) |

TABLE 1-continued

Exocyclic Mimetics Derived from Fas

| Fas Receptor Peptide | | | Exocyclic Mimetic | |
|---|---|---|---|---|
| Designation | Sequence* | | Designation | Sequence |
| Kp3 | 103 CTRTQ 107 | (SEQ ID NO: 18) | Kp3-2 | YCNTRTQNTCY (SEQ ID NO: 12) |
| Kp4 | 69 CQEGKEY 75 | (SEQ ID NO: 19) | Kp4-2 | YCQEKEYCY (SEQ ID NO: 13) |
| | | | Kp4-3 | YCQERKEYCY (SEQ ID NO: 14) |
| Kp7 | 91 CDEGHGL 97 | (SEQ ID NO: 20) | Kp7-2 | YCDEGHLCY (SEQ ID NO: 1) |
| | | | Kp7-3 | YCDEGLCY (SEQ ID NO: 2) |
| | | | Kp7-4 | YCDEGYFCY (SEQ ID NO: 3) |
| | | | Kp7-5 | YCDEGEYCY (SEQ ID NO: 4) |
| | | | Kp7-6 | YCDEHFCY (SEQ ID NO: 5) |
| | | | Kp7-7 | YCDEHGLCY (SEQ ID NO: 6) |
| | | | Kp7-8 | YCDEHGQCY (SEQ ID NO: 7) |
| | | | Kp7-9 | YCDEKFCY (SEQ ID NO: 8) |
| | | | Kp7-10 | YCDEQFCY (SEQ ID NO: 9) |

*Fas amino acid positions are obtained from the amino acid sequence of a full length Fas protein of sequence given in SEQ ID NO: 15.

Example 2

Inhibition of FasL Binding to Fas Receptor

Figure 4:
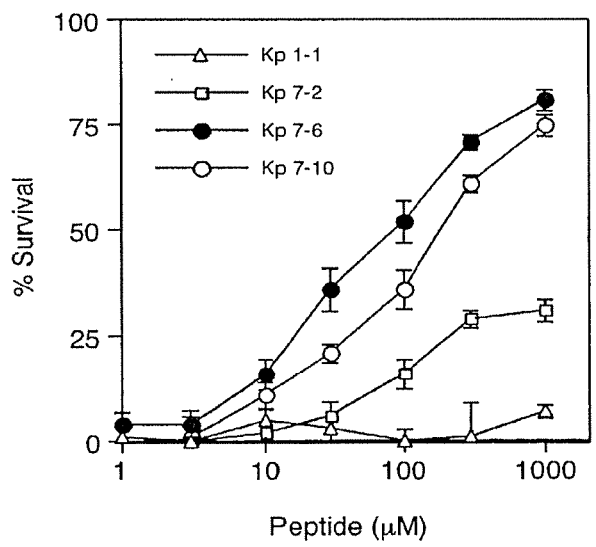
FIG. 4 depicts inhibition of FasL-induced cytolysis in Jurkat cells by the antagonistic peptides.

Fas mimetic activity was evaluated in an assay that measured FasL-Flag binding (100 ng/ml) to Fas-Fc fusion protein immobilized onto plastic plates. The first generation mimetics Kp1-1, 2-2, 3-2, 4-2 and 7-2 were designed from different deduced binding sites of Fas to FasL and screened using a binding inhibition assay comprising 300 µM of peptide and 20 nM of soluble Fas receptor (FIG. 2A). The results indicated that Kp7 loop is a preferred surface for the design of mimetics as a template. Additional generations of exocyclic peptides derived from the Kp7 loop surface were also engineered. By the analysis of the interaction site between FasL and Fas, and biological activity of different mimetics, the aspartic and glutamic acids in Kp7 loop appear to represent the most relevant residues involved in the interaction. However, the particular acidic amino acid at each position is not critical. Hence, for example, either an aspartic acid or a glutamic acid residue can be present at either position. Modification of other residues of Kp7 led to some improvement of inhibitory activities as seen with the Kp7 series (FIG. 2A).

To compare the inhibitory activities of the Kp7 peptide series, dose-response studies were performed. The best activity was found with Kp7-6, which inhibited 50% of the FasL-Flag molecule binding to immobilized Fas-Fc at 150 μM (FIG. 2B).

Example 3

Binding Affinity and Specificity of Kp7 Mimetics

The kinetics of binding of Kp7-6, which mediated the best inhibitory activity to FasL, was performed using surface plasmon resonance (BIAcore™) analysis. FasL-Flag was immobilized onto a sensor chip and various solutions containing different concentrations of Kp7-6 were passed over the surface, FIG. 3A shows the sensogram result obtained with these different Kp7-6 concentrations. The $k_{on}$ and $k_{off}$ rate constants were estimated to be $6.85\times10^{1}\ M^{-1}s^{-1}$ and $7.65\times10^{-4}\ s^{-1}$, respectively, and a $K_D$ of value of $1.12\times10^{-5}$ M was obtained from the ratio of the dissociation/association rate constants. The $k_{off}$ value is considered as an important indicator in the development of therapeutics with biological activity (Benveniste, M. et al. *Br J Pharmacol* 104, 207-221 (1991); Yiallouros, I. et al. *Biochem J* 331, 375-379 (1998)), and generally correlates with potent biological effects. (Moosmayer, D. et al. *J Interferon Cytokine Res* 16, 471-477 (1996)). Although the $K_D$ of the Kp7-6-FasL interaction showed less affinity than that noted for Fas-FasL interactions (Starling, G. C. et al. *J Exp Med* 185, 1487-1492 (1997)), the $k_{off}$ rate was similar with usual antigen-antibody interaction, which suggests that Kp7-6 forms a stable receptor complex and may be useful practically. (Berezov, A. et al. *J Med Chem* 44, 2565-2574 (2001)).

To assess the specificity of Kp7-6 binding interaction, Fas, FasL and TNFα were immobilized on a sensor chip. Kp7-6 bound to FasL but not to TNFα, which indicates Kp7-6 bound to FasL specifically (FIG. 3B). Kp7-6 also bound to Fas (FIG. 3B). This observation is reminiscent of features of the soluble TNF receptor I (p55) which has been shown to form antiparallel homodimeric complexes in the absence of ligand. (Naismith, J. H. et al. *Structure* 4, 1251-1262 (1996)). These results suggest that Fas may also form such antiparallel dimers and the Kp7 loop may contribute to antiparallel dimer formation. No significant binding to TNF-R was detected.

Example 4

Inhibition of FasL-Induced Cytoxicity

To evaluate the effect of mimetics on Fas-mediated cytotoxicity, FasL-sensitive Jurkat cells were stimulated with soluble FasL-Flag fusion protein in the presence or absence of various concentrations of mimetics. The inhibitory effects of mimetics on Fas-mediated cytotoxicity were consistent with the results of the FasL-binding inhibition (FIG. 4). Kp7-6 showed a dose-dependent inhibitory activity. A concentration of 1 mM Kp7-6 protected more than 90% cells from Fas-mediated cytotoxicity (FIG. 4). Kp7-10 also showed a dose-dependent inhibition (FIG. 4). The cyclic peptides did not mediate any cytotoxicity for Jurkat cells in the range of concentration tested (data not shown). Large dose of Kp7-6 was used in this experiment for better signal-to-noise ratio. To determine if mimetics derived from other binding sites would potentially be able to interact synergistically to block the Kp7 surface, Kp7 was used in combination with mimetics. Neither Kp7-6 nor Kp7-10 used in combination with members of the Kp4 mimetics showed any significant synergy, suggesting that inhibition of the Kp7 binding site by itself is sufficient to antagonize FasL activity (data not shown).

Example 5

Inhibition of FasL-Induced Apoptosis

Figure 5:
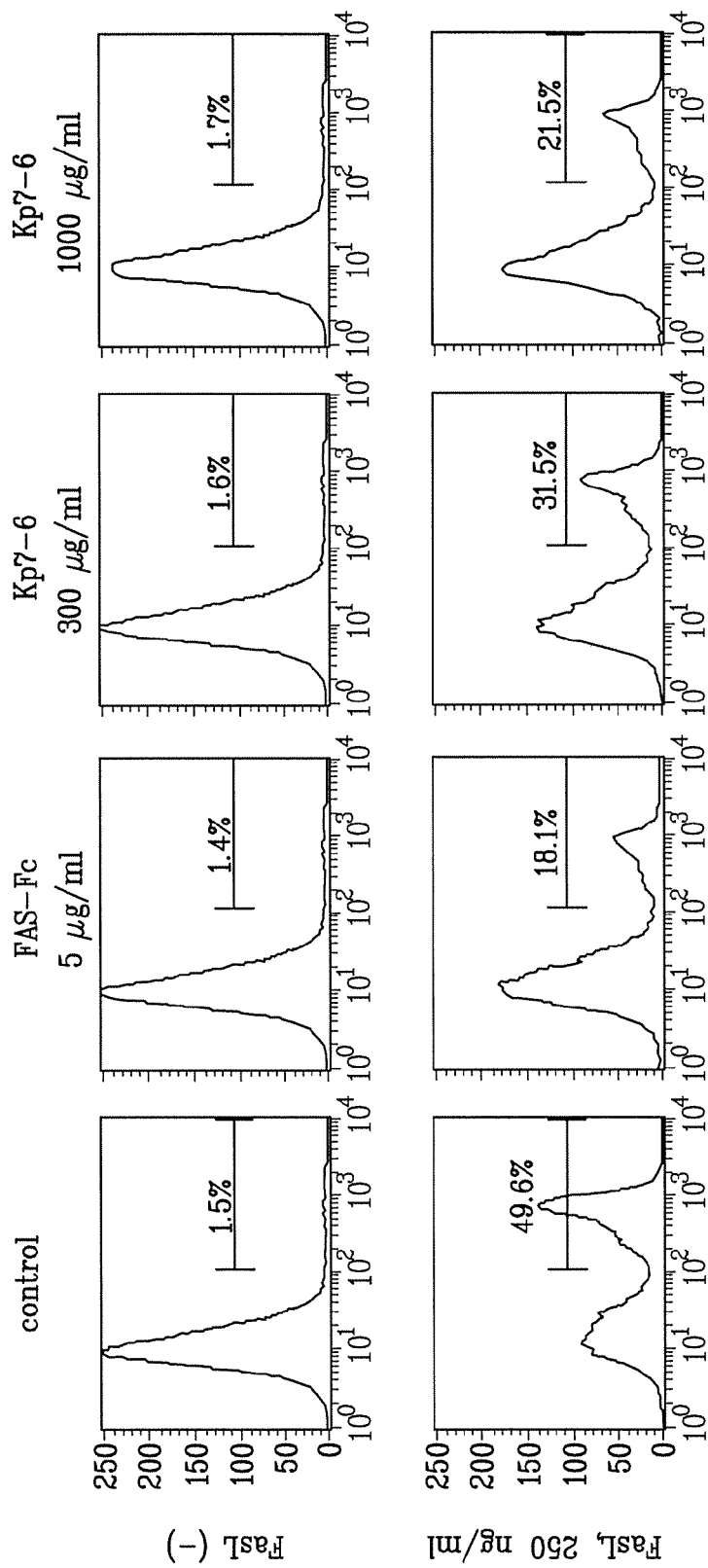
FIG. 5 depicts inhibition of FasL-induced apoptosis in Jurkat cells by the peptide mimetic Kp7-6. The number above the bar in each panel indicates the percentage of apoptotic (annexin-V$^+$) cells.

Biological activity of Fas mimetics was evaluated further by determining the effect of mimetics on Fas-L induced apoptosis. Apoptosis was measured by determining phosphatidylserine (PS) externalization on the cell membrane using annexin V. Translocation of PS to the outer leaflet of the plasma membrane is a common feature of apoptosis and is an early event that can be quantitatively measured using annexin V-FITC binding. Jurkat cells treated with FasL-Flag (200 ng/ml) for 3 h showed a marked increase in PS exposure compared with untreated cells (FIG. 5). The increase in Jurkat cell apoptosis was prevented by Kp7-6 in a dose-dependent manner (FIG. 5).

Example 6

Protection of Mice Against Con A-Induced Injury

Figure 6A:
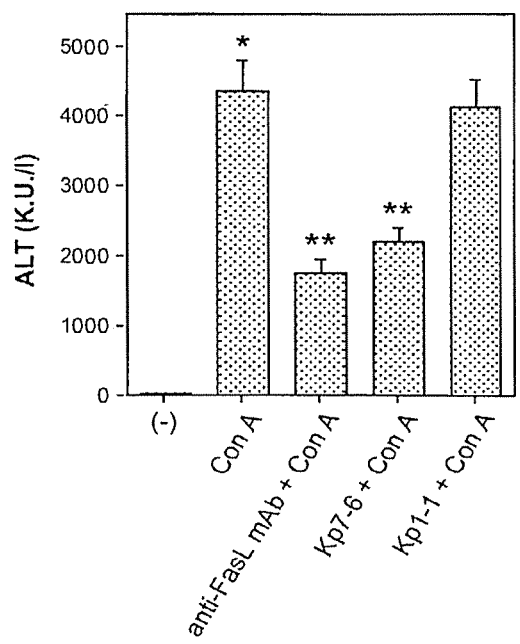
FIG. 6A-B illustrates results showing protection of mice against Con A induced liver injury by the antagonistic Fas mimetic peptide Kp7-7 as measured by serum activities of (A) alanine aminotransferase and (B) aspartate aminotransferase. *P<0.0001 versus control; **P<0.01 versus Con A-treated mice.
Figure 6B:
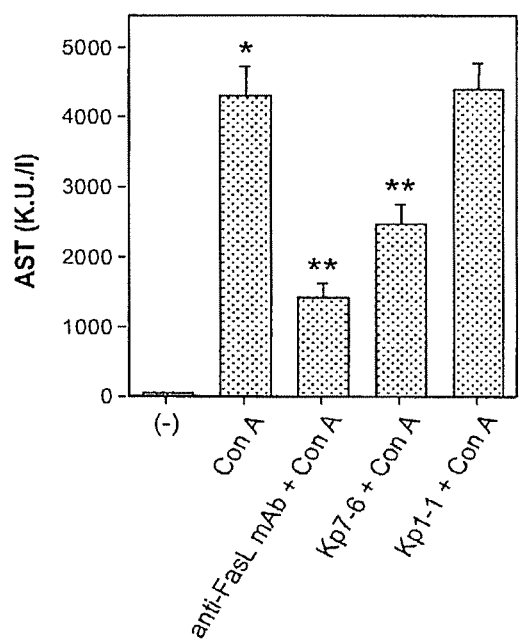

The biological activity of mimetic Kp7-6 was measured in vivo. FasL induced apoptosis is one of the primary and dominant pathways by which liver cells undergo apoptosis under various conditions such as viral infection, drug toxicity and other lesions. (Kakinuma, C. et al. *Toxicol Pathol* 27, 412-420 (1999); Famularo, G., et al. *Med Hypotheses* 53, 50-62 (1999); Gantner et al. supra). Several studies have found that blocking Fas signaling either by RNA interference or by oligonucleotides, will limit the extent of liver damage. (Zhang, H. et al. *Nat Biotechnol* 18, 862-867 (2000); Song, E. et al. *Nat Med* (2003)). The antagonistic effect of Kp7-6 in vivo was tested using the Con A-induced hepatitis model. C57BL/6 mice were pretreated intraperitoneally (IP) with anti-FasL monoclonal antibody, Fas mimetic peptides or saline. After 30 min, animals were challenged intravenously with Con A or saline. The induction of liver damage and inflammatory hepatitis was evaluated by measuring the serum activities of alanine aminotransferase (ALT) and aspartate aminotransferase (AST) 12 h after Con A treatment. The activities of both transaminases were reduced in Kp7-6 pretreated mice (FIG. 6A-B), indicating Kp7-6 blocked Fas-mediated hepatic injury in vivo. Kp1-1 did not block the hepatic injury (FIG. 6A-B). These results were consistent with in vitro data (shown in the preceding examples). Hence, a small rationally designed molecule that can effectively disable Fas receptor functions in vivo.

Suppression of the disease in anti-FasL monoclonal antibody pretreated mice was incomplete, consistent with genetic studies using Fas-deficient lpr/lpr mice, which also showed incomplete suppression of disease in the same Con A-induce hepatitis model. (Tagawa et al. supra). Mechanisms other than that mediated by the Fas-FasL system may also involved in this process.

Example 7

Fas Mimetic Inhibits Angiogenesis in the Eye

Fas Kp7 mimetic was used topically to treat angiogenesis in a mouse eye model. Angiogenesis was induced by placing pellets covered with fibroblast growth factor (FGF) that upon release in the eye lead to blood vessel growth. The degree of neo-vascularization was measured by the diffusion of FITC-dextran from newly formed/neovascularized blood vessels, using routine methods that are well known in the art. See, for example, De Fouw et al., *Microvasc. Res.* 38, 136-147 (1989); Tiedeken & Rovainer, *Microvasc. Res.* 41, 376-389 (1991); Rizzo et al., *Microvasc. Res.* 49, 49-63 (1995). Topical administration of the Fas Kp7 mimetic (1 mg/ml; 3 times/day for 7 days) led to virtual inhibition of new blood vessel formation. Control treatment with a TNF inhibitor also showed no effect.

Example 8

Fas Mimetic Agonist Activity in a Werner Syndrome Cell Line

Fas mimetic activity was further investigated in an assay that measured apoptosis of cells treated with Fas mimetics of the invention. Fas mimetic activity was investigated in two particular cells lines: N6803, an immortalized EBV-transformed human B-lymphoblastoid cell line (Kataoka et al., *Differentiation* 62, 203-211 (1997)), and WS10201, an EBV-transformed B-lymphoblastoid cell line derived from a Werner syndrome patient (see, Okada et al., *Biol. Pharm. Bull.* 21, 235-239 (1998); Hanma et al., *Mutat. Res.* 520, 15-24 (2002)). Werner syndrome is a recessive genetic disorder that causes premature aging and an enhanced risk of rare cancers (see, Goto et al., *Hum. Genet.* 105, 301-307 (1999)).

Live cells were separated by lymphocyte separation medium in cultured in wells of a 96-well plate ($10^5$ cells per well) for sixteen hours in the presence of an agonistic anti-Fas IgM antibody. Such antibodies are commercially available, e.g., from Beckman Coulter (Fullerton, Calif.). Cell were incubated either with anti-Fas IgM antibody alone or with the Fas mimetic Kp7-6 at doses of 10, 100 and 1000 ng/ml. A control group of cells was also incubated in culture medium alone (i.e., no anti-Fas IgM or Fas mimetic) under the same conditions. Apoptosis was assessed by TUNEL method (Gavrieli et al., *J. Cell Biol.* 119, 493-501 (1992); Gorczyca et al., *Cancer Res.* 53, 1945-1951 (1993); see, also, Ausubel et al. (Eds.) in *Current Protocols in Molecular Biology*, at page 14.13.15).

Figure 7A:
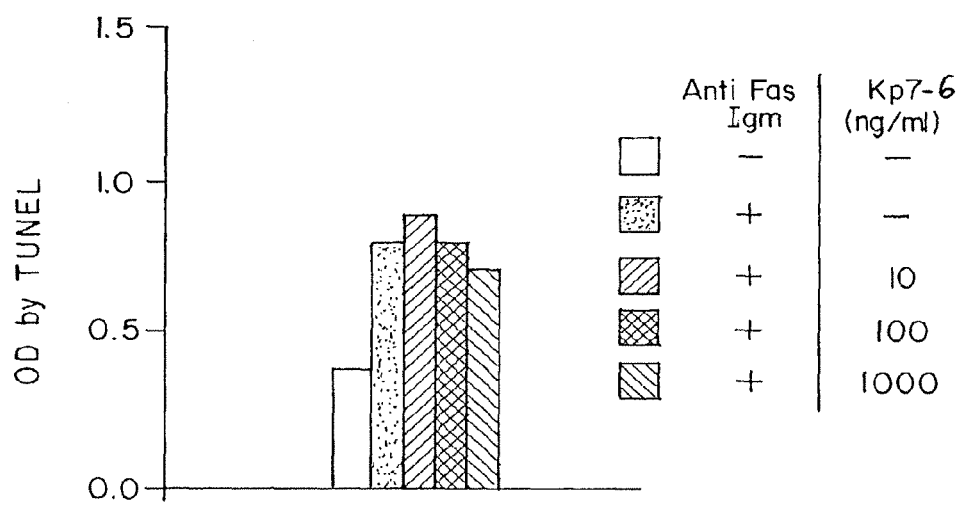
FIG. 7A-B shows apopotosis levels measured in (A) N6803 cells and (B) WS10201 cells treated with anti-Fas IgM antibody and Fas mimetic Kp7-6.
Figure 7B:
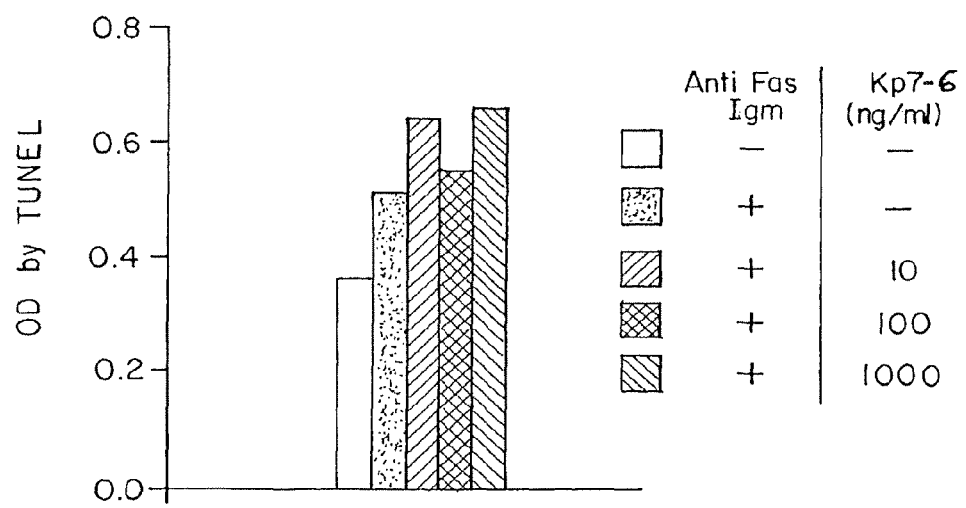

FIG. 7A-7B plots the apoptosis levels measured in N6803 and WS10201 cells, respectively. As expected, incubation of the cell lines with anti-Fas IgM increased apoptosis compared to cells incubated in medium along. Incubation with both anti-Fas IgM and Fas mimetic did not significantly alter apoptosis in the N6803 cell line compared to incubation with anti-Fas IgM along (FIG. 7A). However, Fas mimetic exhibited a synergistic effect with anti-Fas IgM in the WS10201 cell line, greatly enhancing apoptosis compared to treatment with anti-Fas IgM in the absence of Fas mimetic (FIG. 7B).

These data show that Fas mimetic of the invention can stimulate apoptosis in these circumstances, suggesting an agonistic effect in certain conditions. In particular, and without being limited by any particular theory or mechanism of action, receptors such as Fas are believed to exists in two states (see, Lef, *Trends Pharmacol. Sci.* 16, 89-97 (1995)): an inactive monomer form and an active, signal competent dimer. At low concentrations, such as the concentrations used in these experiments, Fas mimetic is believed to bind to the signal competent dimer form of Fas but does not shift the receptor population to the inactive monomer state. In these conditions, particularly in the absence of FasL, Fas mimetics of the invention are expected to exhibit at least a transient stimulation of Fas activity and so have an agonistic effect. At higher concentrations, however, Fas mimetics are believed to shift equilibrium of Fas to the signal incompetent monomer form, thereby inhibiting Fas signal and so having an antagonistic effect. Such "inverse agonist" properties are known in the art and have been described for peptide mimetics of other receptors, such as the CD4 receptor. See, for example, Horie et al., *Exp. Mol. Pathol.* 73, 93-103 (2002).

Example 9

Experimental Protocols

Materials. Human recombinant TNFα was obtained from Roche Diagnostics (Indianapolis, Ind.). Flag-tagged soluble human Fas ligand (FasL-Flag) and human Fas extra cellular domain-LgGFc fusion protein (Fas-Fc) were purchased from Kamiya Biomedical (Seattle, Wash.). Human recombinant TNF-receptor (I) extracellular domain-IgGFc fusion protein (TNFRI-Fc) was obtained from R & D systems (Minneapolis, Minn.). Anti-Flag-HRP antibody, hydrogen peroxide solution, 3,3',5,5'-tetramethylbenzidine (TMBZ) and concanavalin A were from Sigma Biochemical Co. (St. Louis, Mo.).

Cell lines. American Type Culture Collection Jurkat cells were grown in RPMI 1640 medium supplemented with 10% heat inactivated fetal calf serum, L-glutamine (2 mM), penicillin (100 U/ml) and streptomycin (100 μg/ml) at 37° C. in a humidified 5% CO2 atmosphere.

Mice. Eight-week-old C57BL/6 (B6) mice were purchased from CLEA JAPAN Inc. (Tokyo, Japan). All mice used were maintained under specific pathogen-free conditions in our animal facility.

Molecular Modeling. Computer modeling and the structural analysis were performed using both QUANTA and INSIGHT (Molecular Simulation, San Diego, Calif.). The model peptides designed were constructed from their sequences and folding using CHARMM. The side chain of amino acid residues were first positioned to permitted conformation using the Ponders rotamer (Ponder, J. W. et al. *J Mol Biol* 193, 775-791 (1987)) database provided in QUANTA. Then the folded peptides were minimized to convergence with a dielectric constant set to 80. The molecular model of the human Fas/FasL complex was built by using Modeller 3.0 (Sali, A. et al. *J Mol Biol* 212, 403-428 (1990); Sali, A. et al. *Trends in Biochem Sci* 15, 235-240 (1990)) using the crystal structure of TNF receptor and molecular model of Fas (Bajorath supra) from Brookhaven database. (Bernstein, F. C. et al. *J Mol Biol* 112, 535-542 (1977)). The conformation of loops were constructed using both loop search algorithm and CONGEN. (Bruccoleri, R. E. et al. *Nature* 335, 564-568 (1988)). The quality of the model were assessed using Ramachandran plot (for phi, psi violations) and profile analysis.

(Zhang et al. supra). The Fas/FasL complex was optimized using rigid body minimization using XPLOR3.1 (Brünger, A. T. X-PLOR. Version 3.1. A System for X-ray Crystallography and NMR. (Yale University Press, New Haven, Conn., 1992)) and INSIGHT.

Mimetics were designed from essential sequences of Fas-FasL interactions. About five to seven amino acid sequences of Fas, have been used to mimic the conformation of loops Kp1 to Kp7 as shown in Table 1.

Peptide synthesis and cyclization. Peptides were synthesized by solid-phase methods, deprotected, and released from the resin using anhydrous HF. Peptides were lyophilized and further purified by HPLC utilizing a C18 column and then relyophilized. Peptides were more than 95% pure by HPLC analysis and mass spectrometry.

The peptides containing internal cysteine residues were refolded and oxidized as described previously. (Takasaki et al. supra). Briefly, peptides were dissolved at 100 μg/ml in distilled water adjusted to pH 8.0 by $(NH_4)_2CO_3$ and stirred at 4° C. until 95% formation of intramolecular disulfide bonds had been confirmed by DTNB (Sigma Biochemical Co., St. Louis, Mo.). The cyclized peptides were lyophilized and analyzed for purity by HPLC. These peptides showed greater than 90% purity by HPLC analysis.

Solid phase ligand binding assay. Fas-Fc fusion protein (250 ng/ml) diluted in PBS was immobilized onto 96 well ELISA plate (Costar, High Wycombe, UK) by incubating overnight at 4° C. After blocking with PBS containing 1% skim milk overnight at 4° C. and subsequent washing with PBS containing 0.05% Tween 20 (PBS-Tw), Flag-tagged soluble FasL (100 ng/ml)/peptide solution preincubated in PBS containing 1% skim milk for 1 h at 37° C. was added onto the Fas-Fc coated wells. After 2 h incubation at room temperature, the plate was washed with PBS-Tw, and anti-FLAG (M2)-HRP antibody 1:2500 in PBS containing 1% skim milk was added. After 1 h incubation at room temperature, the plate was washed with PBS-Tw, and the enzyme reaction was started by adding the substrate solution (0.1M sodium acetate buffer (pH 5.0) containing 100 g/ml of TMBZ and 0.005% (v/v) $H_2O_2$) and stopped with $2NH_2SO_4$. The absorbance at 450 nm was measured with an ELISA reader.

Biosensor analysis. All experiments were carried out on a BIAcore 3000 instrument (Biacore AG, Uppsala, Sweden) at 25° C. using PBS, pH 7.4, containing 0.005% surfactant P20 (Biacore AG) as the running buffer. FasL-Flag, Fas-Fc or TNFRI-Fc was immobilized on research-grade CM5 sensor chips (Biacore AG) using standard N-ethyl-N-dimethylaminopropyl carbodiimid/N-hydroxysuccinimide coupling. Immobilization was performed in 10 mM sodium acetate buffer at pH 4.5 for FasL-Flag and Fas-Fc, and at pH 4.0 for TNFRI-Fc. After coupling, excess N-hydroxysuccinimide groups were inactivated with ethanolamine. For binding studies, about 1500 resonance units (RU) of FasL-Flag, Fas-Fc and TNFRI-Fc were coupled to the chips. Surface plasmon resonance (SPR) measurements were carried out at a flow rate of 20 ml min$^{-1}$. Data were analyzed with the BIA evaluation 3.0 software (Biacore AG). The sensograms give values for the relative response in resonance units (RU) after background subtraction versus time in seconds. The association phase injection time was 300 seconds followed by dissociation buffer.

Cytotoxicity assay. Twenty microliters of Jurkat cells at $1 \times 10^5$ cells/ml were plated in 96-well U-bottom plates. FasL-Flag (120 ng/ml in culture medium) was preincubated with equal volume of peptide sample in PBS for 1 h at 37° C., and 20 μl of mixture was added to each well. After an incubation period of 24 h, each culture was pulsed with 1 μCi of [$^3$H]- thymidine for 24 h before harvesting on glass fiber filters. Incorporation of the $^3$H-thymidine obtained with culture medium alone and with 30 ng/ml of FasL was used as reference for 100% survival and 0% survival, respectively. Survival (%) by several doses of peptides was plotted. Incorporation of the radioactive label was measured by liquid scintillation counting (Wallac, Finland) and expressed as the arithmetic mean counts per minute (cpm) of triplicate cultures.

Flow cytometry assay for apoptosis. Apoptotic cells were detected by annexin V-FITC binding to phosphatidylserine (PS) expressed on the cell membrane in the early phase of apoptosis using a commercial kit purchased from Roche (Indianapolis, Ind.). Briefly, 1×10$^5$ Jurkat cells were cultured with FasL-Flag (250 ng/ml) in the presence or absence of peptide sample for 3 h. The cells were then washed with PBS and resuspended in 100 µl of binding buffer containing optimal concentration of calcium, FITC-conjugated annexin V and propidium iodide (PI) for 10 min. at room temperature. After adding an additional 400 µl of binding buffer, cells were analyzed by FACScan (Becton Dickinson Immunocytometry Systems, San Jose, Calif.). CELLQuest software programs (Becton Dickinson Immunocytometry Systems, San Jose, Calif.) were used for collecting and analyzing data. Early apoptotic cells were expressed as percentage of cells positive for annexin V and negative for PI. 10,000 cells were analyzed in each condition.

Administration of Con A and Measurement of Serum Transaminase Activity. Hepatic damage was induced by injection of a single dose of 0.5 mg Con A dissolved in pyrogen-free saline and administered to mice via the tail vein. Anti-FasL monoclonal antibody (MFL-4; Kayagaki, N. et al. *Proc Natl Acad Sci USA* 94, 3914-3919 (1997)) or Fas mimetic peptide (Kp7-6 or Kp1-1) was diluted with pyrogen-free saline and injected in a single dose intraperitoneally 30 minutes before Con A.

Blood samples were collected from mice at 12 h after Con A injection, and the serum was taken by centrifugation. Serum activities of alanine aminotransferase (ALT) and aspartate aminotransferase (AST) were measured by Lippi-Guidi's method (Iatrozyme TA-LQ: Dia-Iatron Inc., Tokyo, Japan). (Lippi, U. et al. *Clin Chim Acta* 28, 431-437 (1970)).

Statistical analysis. Results are expressed as mean±SE, and analyzed by the Student's t test or analysis of variance (ANOVA) where appropriate. Post hoc comparisons were performed using Scheffe test. A 95% confidence interval was used to define statistical significance.

REFERENCES CITED

Numerous references, including patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entirety and to the same extent as if each reference was individually incorporated by reference.

What is claimed is:

1. A method of treating a FAS-related pathology comprising administering to a mammal suffering from said FAS-related pathology a therapeutically effective amount of a Fas mimetic represented by the formula (I)

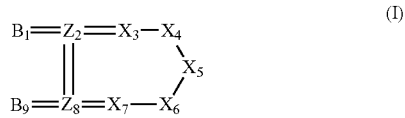

wherein $B_1$ and $B_9$ are independently a peptide of 1-6 genetically encoded amino acids, at least one of which is a genetically encoded hydrophobic amino acid, or a genetically encoded aromatic amino acid, $Z_2$ is cysteine, that forms a covalent linkage with $B_1$, $X_3$ or $X_4$ and $Z_8$, $Z_8$ is cysteine, that forms a covalent linkage with $B_9$, $X_7$ and $Z_2$, $X_3$ is a genetically encoded hydrophilic amino acid or null, $X_4$ is aspartic acid or glutamic acid, $X_5$ is aspartic acid or glutamic acid, $X_6$ is selected from the group consisting of histidine, lysine, arginine, asparagine or glutamine, $X_7$ is a genetically encoded aromatic amino acid, "—" is a covalent linkage comprising an amide or a substituted amide thereof, and "=" is a covalent linkage, or a pharmaceutically acceptable salt thereof, wherein said FAS-related pathology is selected from the group consisting of rheumatoid arthritis, Sjogren's syndrome, multiple sclerosis, hepatitis, retinal neovascularization, corneal neovascularization, renal injury, graft rejection, HIV infection and macular degeneration.

2. The method of claim 1 wherein said FAS-related pathology is selected from the group consisting of hepatitis and renal injury.

3. The method of claim 1 wherein said mammal is a human.

4. The method of claim 1 wherein said mimetic is administered as a pharmaceutically acceptable composition.

5. The method of claim 3 wherein said mimetic is administered via an oral, parenteral, intranasal, sublingual, rectal or inhalatory route, or by insufflation, transdermal patches or lyophilized composition.

6. The method of claim 5 wherein said mimetic is administered in an amount of between about 0.01 to about 25 mg/kg/day.

7. The method of claim 6 wherein said mimetic is administered in an amount of between about 0.1 to about 10 mg/kg/day.

8. The method of claim 7 wherein said mimetic is administered in an amount of about 0.2 to about 5 mg/kg/day.

9. The method of claim 5 wherein said mimetic is administered at a total daily dose of about 25 to about 1000 mg.

10. The method of claim 9 wherein said mimetic is administered at a total daily dose of about 150 to about 500 mg.

11. The method of claim 9 wherein said mimetic is administered at a total daily dose of about 350 mg.

12. A method of treating a FAS-related pathology comprising administering to a mammal suffering from said FAS-related pathology a therapeutically effective amount of a Fas mimetic having an amino acid sequence selected from the group consisting of YCDEGHLCY (SEQ ID NO:1); YCDE- GLCY (SEQ ID NO:2); YCDEGYFCY (SEQ ID NO:3); YCDEGEYCY (SEQ ID NO:4); YCDEHFCY (SEQ IN NO:5); YCDEHGLCY (SEQ ID NO:6); YCDEHGQCY (SEQ ID NO:7); YCDEKFCY (SEQ ID NO:8); YCDEQFCY (SEQ ID NO:9); YCNSTVCY (SEQ ID NO:10); YCDKAEHFCY (SEQ ID NO:11); YCNTRTQNTCY (SEQ ID NO:12); YCQEKEYCY (SEQ ID NO:13); and YCQERKEYCY (SEQ ID NO:14)

wherein said FAS-related pathology is selected from the group consisting of, rheumatoid arthritis, Sjogren's syndrome, multiple sclerosis, hepatitis, retinal neovascularization, corneal neovascularization, renal injury, graft rejection, HIV infection and macular degeneration.

13. The method of claim 12 wherein said FAS-related pathology is selected from the group consisting of hepatitis and renal injury.

14. The method of claim 12 wherein said mammal is a human.

15. The method of claim 12 wherein said mimetic is administered as a pharmaceutically acceptable composition.

16. The method of claim 14 wherein said mimetic is administered via an oral, parenteral, intranasal, sublingual, rectal or inhalatory route, or by insufflation, transdermal patches or lyophilized composition.

17. The method of claim 16 wherein said mimetic is administered in an amount of between about 0.01 to about 25 mg/kg/day.

18. The method of claim 17 wherein said mimetic is administered in an amount of between about 0.1 to about 10 mg/kg/day.

19. The method of claim 18 wherein said mimetic is administered in an amount of about 0.2 to about 5 mg/kg/day.

20. The method of claim 16 wherein said mimetic is administered at a total daily dose of about 25 to about 1000 mg.

21. The method of claim 20 wherein said mimetic is administered at a total daily dose of about 150 to about 500 mg.

22. The method of claim 20 wherein said mimetic is administered at a total daily dose of about 350 mg.

\* \* \* \* \*

UNITED STATES PATENT AND TRADEMARK OFFICE
CERTIFICATE OF CORRECTION

Page 1 of 1

PATENT NO. : 8,680,047 B2
APPLICATION NO. : 13/210117
DATED : March 25, 2014
INVENTOR(S) : Mark I. Greene, Ramachandran Murali and Akihiro Hasegawa It is certified that error appears in the above-identified patent and that said Letters Patent is hereby corrected as shown below:

Title Page,
In the Title (54), delete the misprint of the title as it appears on the title page and insert
-- FAS PEPTIDE MIMETICS AND USES THEREOF --.

In the Specification

Column 25,
Line 32, delete "domain-LgGFc" and insert -- domain-IGGFc --.

Column 26,
Line 39, delete "100 g/ml" and insert -- 100 µg/ml --.

In the Claims

Column 37,
Claim 12, Line 2, delete "(SEQ IN" and insert -- (SEQ ID --.

Signed and Sealed this
Tenth Day of March, 2015

Michelle K. Lee
*Deputy Director of the United States Patent and Trademark Office*

SEQUENCE LISTING

```
<160> NUMBER OF SEQ ID NOS: 20

<210> SEQ ID NO 1
<211> LENGTH: 9
<212> TYPE: PRT
<213> ORGANISM: Artificial Sequence
<220> FEATURE:
<223> OTHER INFORMATION: Synthetic construct

<400> SEQUENCE: 1

Tyr Cys Asp Glu Gly His Leu Cys Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic construct

<400> SEQUENCE: 2

Tyr Cys Asp Glu Gly Leu Cys Tyr
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic construct

<400> SEQUENCE: 3

Tyr Cys Asp Glu Gly Tyr Phe Cys Tyr
1               5
```

```
<210> SEQ ID NO 4
<211> LENGTH: 9
<212> TYPE: PRT
<213> ORGANISM: Artificial Sequence
<220> FEATURE:
<223> OTHER INFORMATION: Synthetic construct

<400> SEQUENCE: 4

Tyr Cys Asp Glu Gly Glu Tyr Cys Tyr
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic construct

<400> SEQUENCE: 5

Tyr Cys Asp Glu His Phe Cys Tyr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic construct

<400> SEQUENCE: 6

Tyr Cys Asp Glu His Gly Leu Cys Tyr
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic construct

<400> SEQUENCE: 7

Tyr Cys Asp Glu His Gly Gln Cys Tyr
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic construct

<400> SEQUENCE: 8

Tyr Cys Asp Glu Lys Phe Cys Tyr
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic construct

<400> SEQUENCE: 9

Tyr Cys Asp Glu Gln Phe Cys Tyr
1               5
```

```
<210> SEQ ID NO 10
<211> LENGTH: 8
<212> TYPE: PRT
<213> ORGANISM: Artificial Sequence
<220> FEATURE:
<223> OTHER INFORMATION: Synthetic construct

<400> SEQUENCE: 10

Tyr Cys Asn Ser Thr Val Cys Tyr
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic construct

<400> SEQUENCE: 11

Tyr Cys Asp Lys Ala Glu His Phe Cys Tyr
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic construct

<400> SEQUENCE: 12

Tyr Cys Asn Thr Arg Thr Gln Asn Thr Cys Tyr
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Synthetic construct

<400> SEQUENCE: 13

Tyr Cys Gln Glu Lys Glu Tyr Cys Tyr
1               5

<210> SEQ ID NO 14
<211> LENGTH: 10
<212> TYPE: PRT
<213> ORGANISM: Artificial Sequence
<220> FEATURE:
<223> OTHER INFORMATION: Synthetic construct

<400> SEQUENCE: 14

Tyr Cys Gln Glu Arg Lys Glu Tyr Cys Tyr
1               5                   10

<210> SEQ ID NO 15
<211> LENGTH: 319
<212> TYPE: PRT
<213> ORGANISM: Artificial Sequence
<220> FEATURE:
<223> OTHER INFORMATION: Synthetic construct

<400> SEQUENCE: 15

Arg Leu Ser Ser Lys Ser Val Asn Ala Gln Val Thr Asp Ile Asn Ser
1               5                   10                  15

Lys Gly Leu Glu Leu Arg Lys Thr Val Thr Thr Val Glu Thr Gln Asn
                20                  25                  30
```

```
Leu Glu Gly Leu His His Asp Gly Gln Phe Cys His Lys Pro Cys Pro
            35                  40                  45

Pro Gly Glu Arg Lys Ala Arg Asp Cys Thr Val Asn Gly Asp Glu Pro
 50                  55                  60

Asp Cys Val Pro Cys Gln Glu Gly Lys Glu Tyr Thr Asp Lys Ala His
 65                  70                  75                  80

Phe Ser Ser Lys Cys Arg Arg Cys Arg Leu Cys Asp Glu Gly His Gly
                85                  90                  95

Leu Glu Val Glu Ile Asn Cys Thr Arg Thr Gln Asn Thr Lys Cys Arg
            100                 105                 110

Cys Lys Pro Asn Phe Phe Cys Asn Ser Thr Val Cys Glu His Cys Asp
            115                 120                 125

Pro Cys Thr Lys Cys Glu His Gly Ile Ile Lys Glu Cys Thr Leu Thr
130                 135                 140

Ser Asn Thr Lys Cys Lys Glu Glu Gly Ser Arg Ser Asn Leu Gly Trp
145                 150                 155                 160

Leu Cys Leu Leu Leu Leu Pro Ile Pro Leu Ile Val Trp Val Lys Arg
                165                 170                 175

Lys Glu Val Gln Lys Thr Cys Arg Lys His Arg Lys Glu Asn Gln Gly
            180                 185                 190

Ser His Glu Ser Pro Thr Leu Asn Pro Glu Thr Val Ala Ile Asn Leu
            195                 200                 205

Ser Asp Val Asp Leu Ser Lys Tyr Ile Thr Thr Ile Ala Gly Val Met
210                 215                 220

Thr Leu Ser Gln Val Lys Gly Phe Val Arg Lys Asn Gly Val Asn Glu
225                 230                 235                 240

Ala Lys Ile Asp Glu Ile Lys Asn Asp Asn Val Gln Asp Thr Ala Glu
                245                 250                 255

Gln Lys Val Gln Leu Leu Arg Asn Trp His Gln Leu His Gly Lys Lys
            260                 265                 270

Glu Ala Tyr Asp Thr Leu Ile Lys Asp Leu Lys Lys Ala Asn Leu Cys
            275                 280                 285

Thr Leu Ala Glu Lys Ile Gln Thr Ile Ile Leu Lys Asp Ile Thr Ser
            290                 295                 300

Asp Ser Glu Asn Ser Asn Phe Arg Asn Glu Ile Gln Ser Leu Val
305                 310                 315

<210> SEQ ID NO 16
<211> LENGTH: 6
<212> TYPE: PRT
<213> ORGANISM: Artificial Sequence
<220> FEATURE:
<223> OTHER INFORMATION: Synthetic construct

<400> SEQUENCE: 16

Cys Asn Ser Thr Val Cys
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic construct

<400> SEQUENCE: 17

Asp Lys Ala His Phe Ser Ser Lys Cys
1               5
```

```
<210> SEQ ID NO 18
<211> LENGTH: 5
<212> TYPE: PRT
<213> ORGANISM: Artificial Sequence
<220> FEATURE:
<223> OTHER INFORMATION: Synthetic construct

<400> SEQUENCE: 18

Cys Thr Arg Thr Gln
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic construct

<400> SEQUENCE: 19

Cys Gln Glu Gly Lys Glu Tyr
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic construct

<400> SEQUENCE: 20

Cys Asp Glu Gly His Gly Leu
1               5
```